US011166631B2

(12) United States Patent
Fukuma et al.

(10) Patent No.: US 11,166,631 B2
(45) Date of Patent: Nov. 9, 2021

(54) OPHTHALMOLOGIC MICROSCOPE AND FUNCTION EXPANSION UNIT

(71) Applicant: Topcon Corporation, Tokyo (JP)

(72) Inventors: Yasufumi Fukuma, Tokyo (JP); Kazuhiro Oomori, Tokyo (JP)

(73) Assignee: Topcon Corporation, Tokyo (JP)

( * ) Notice: Subject to any disclaimer, the term of this patent is extended or adjusted under 35 U.S.C. 154(b) by 252 days.

(21) Appl. No.: 16/616,564

(22) PCT Filed: May 25, 2018

(86) PCT No.: PCT/JP2018/020084
§ 371 (c)(1),
(2) Date: Nov. 25, 2019

(87) PCT Pub. No.: WO2018/216788
PCT Pub. Date: Nov. 29, 2018

(65) Prior Publication Data
US 2020/0077889 A1    Mar. 12, 2020

(30) Foreign Application Priority Data

May 25, 2017  (JP) .............................. JP2017-103242
Aug. 30, 2017  (JP) .............................. JP2017-165187
Mar. 23, 2018  (JP) .............................. JP2018-057091

(51) Int. Cl.
*A61B 3/135*    (2006.01)
*A61B 3/10*    (2006.01)
(52) U.S. Cl.
CPC .............. *A61B 3/135* (2013.01); *A61B 3/102* (2013.01)

(58) Field of Classification Search
CPC ......... A61B 3/135; A61B 3/102; A61B 3/132; A61B 3/0058; A61B 3/0025; A61B 3/1025
(Continued)

(56) References Cited

U.S. PATENT DOCUMENTS 4,699,481 A * 10/1987 Matsumura ............ A61B 3/135
351/205
8,366,271 B2    2/2013 Izatt et al.
(Continued)

FOREIGN PATENT DOCUMENTS

JP    H8-066421      6/2006
JP    2010-522055    2/2008
(Continued)

*Primary Examiner* — Mohammed A Hasan
(74) *Attorney, Agent, or Firm* — BakerHostetler

(57) ABSTRACT

The object of the present invention is to develop an ophthalmologic microscope of a new method that increases the degree of freedom in the optical design in the Galilean ophthalmologic microscope provided with an OCT optical system. The present invention provides an ophthalmologic microscope, wherein an observation optical system, an objective lens, and an OCT optical system are placed in such a way that the optical axis of the OCT optical system does not penetrate through objective lens, and the optical axis of the observation optical system and the optical axis of the OCT optical system are non-coaxial, and wherein the ophthalmologic microscope further comprises a SLO optical system that scans a light ray which is a visible ray, a near infrared ray, or an infrared ray and guides the light to the subject's eye so as to become substantially coaxial with the optical axis of the OCT optical system.

5 Claims, 18 Drawing Sheets

(58) Field of Classification Search
USPC .......................................................... 351/221
See application file for complete search history.

(56) References Cited

U.S. PATENT DOCUMENTS

| 2012/0092615 | A1 | 4/2012 | Izatt et al. |
| 2012/0184846 | A1 | 7/2012 | Izatt et al. |
| 2018/0184897 | A1 | 7/2018 | Yamamoto et al. |

FOREIGN PATENT DOCUMENTS

| JP | 2008-264488 | | 11/2008 |
| JP | 2008-264490 | | 11/2008 |
| JP | 2008-268852 | | 11/2008 |
| JP | 2015-221091 | | 12/2015 |
| JP | 2016-185177 | | 10/2016 |
| JP | 2016-185178 | | 10/2016 |
| JP | 2018196676 | A * | 12/2018 |
| WO | 2017002381 | A1 | 1/2017 |

* cited by examiner

OPHTHALMOLOGIC MICROSCOPE AND FUNCTION EXPANSION UNIT

RELATED APPLICATIONS

The present U.S. Patent Application is a U.S. national-phase application under 35 U.S.C. § 371 of International Application No. PCT/JP2018/020084 filed on May 24, 2018. This present application claims priority under 35 U.S.C. § 119 and the Paris Convention for the Protection of Industrial Property to Japanese Patent Application No. 2017-103242, filed May 25, 2017; Japanese Patent Application No. 2017-165187, filed Aug. 30, 2017; and Japanese Patent Application 2018-057091, filed Mar. 23, 2018. The entire disclosures of the foregoing Japanese Patent Applications and International Application No. PCT/JP2018/020084 are incorporated herein by reference.

TECHNICAL FIELD

The present invention relates to an ophthalmologic microscope comprising an illuminating optical system for illuminating a subject's eye and an observation optical system for observing the subject's eye, such as a fundus camera, a slit lamp, a microscope for ophthalmic surgery. The inventive ophthalmologic microscope is characterized in that it comprises an OCT optical system capable of obtaining tomographic images of the subject's eye with Optical Coherence Tomography (abbreviated as OCT) and that the OCT optical system and an observation optical system can be independent from one another, and this can increase the degree of freedom in the design for ophthalmologic microscope.

The invention also relates to a function expansion unit detachable to the ophthalmologic microscope and capable of adding functions of OCT to the ophthalmologic microscope.

BACKGROUND ART

An ophthalmologic microscope is a medical or inspection equipment that illuminates a subject's eye of a patient with an illuminating optical system and enlarges it to observe with an observation optical system consisting of lens, etc. Such ophthalmologic microscopes that can obtain tomographic images of the subject's eye due to inclusion of an OCT optical system have been developed.

OCT is a technique that constitutes an interferometer using a low coherence (a short coherence length) light source, thereby obtains tomographic images of a biological body. In particular, it uses the low coherence light source, divides its light in half with a beam splitter, irradiates one of the lights (a measuring light) to the biological tissue to reflect or scatter, and reflects the other of the lights (a reference light) with a mirror. The measuring light is reflected or scattered at a variety of depth of the biological tissue and numerous reflected or scattered light return. After converging the measuring light returned to the beam splitter and the reflected light of the reference light, only the reflected or scattered light of the measuring light which went through the same distance as the reference light is detected interfering with the reflected light of the reference light. Therefore, intensities of the measuring light reflected at the various depth of the biological tissue can be detected by adjusting positions of the beam splitter and the mirror to variously change the path length of the reference light. With such OCT optical system, tomographic images of a biological tissue can be obtained.

Providing this OCT optical system on an ophthalmologic microscope enabled to obtain tomographic images of a retina and cornea of eye, iris, etc. and enabled to observe not only the surface but also internal condition of tissues. This can improve diagnostic accuracy of eye diseases, and also improve the success rate in ophthalmic surgery.

For the ophthalmologic microscope comprising such OCT optical system, there is a need to incorporate the OCT optical system into the microscope comprising the illuminating optical system and the observation optical system such that the light of the OCT optical system can enter a subject's eye, and various methods have been developed.

For example, for a Galilean ophthalmologic microscope that comprises an observation optical system consisting of observation optical systems for left and right eyes of an observer, and comprises one objective lens through which the optical axes of the observation optical systems for left and right eyes commonly penetrate, there is a method that makes the light of OCT light source entered from the side of the objective lens reflect directly above the objective lens with a reflecting member and then penetrate through the objective lens to enter the subject's eye (Patent documents 1 and 2, etc.).

Explaining more fully, as shown in FIG. 17 (a drawing citied from FIG. 1 of Patent document 1), the ophthalmologic microscope comprises an observation optical system consisting of lens groups 130, 140, 150, 170, 180, that are pairs of left and right through which the optical axis of the observation optical system for left eye and the optical axis of the observation optical system for right eye penetrate respectively, one objective lens 110 through which the optical axis of the observation optical system for left eye and the optical axis of the observation optical system for right eye commonly penetrate, OCT optical systems 200, 250, 450, 460, 470, and illuminating optical systems 310, 320, 330. In the OCT optical system, the output light from the OCT light source 200 is emitted through an optical fiber 250, converged with the illuminating light from the illuminating optical system at a beam combiner 340 after being controlled its direction by two scanning mirrors 450, 460, and reflected at splitter 120 to enter a subject's eye 1000.

Yet, for the Galilean ophthalmologic microscope, there is a method that makes the light of the OCT light source emit from the upper side of the objective lens, penetrate through the objective lens, and enter a subject's eye (Patent document 3).

Moreover, for the Galilean ophthalmologic microscope, there is a method that makes the light path of the OCT optical system converge substantially coaxially with the light path of the observation optical system, penetrate the objective lens, and enter a subject's eye (Patent documents 4 and 5).

All methods described above are ones that the optical axis of the observation optical system and the optical axis of the OCT optical system commonly penetrate through one objective lens.

For the Galilean ophthalmologic microscope, as a method that the optical axis of the OCT optical system does not penetrate through objective lens, there is a method that makes the light of OCT light source entered from the side of the objective lens reflect directly under the objective lens with a reflecting member, and enter a subject's eye without penetrating through the objective lens (Patent document 6).

Explaining more fully, as shown in FIG. 18 (a drawing cited from FIG. 2A of Patent document 6), at the lower side of the objective lens 102 through which the optical axis of the observation optical system penetrates, the light of the OCT light source entered from the side of the objective lens is reflected at a dichroic mirror 400, and the light of the OCT optical system enters a subject's eye.

In this method, the light path of the observation optical system and the light path of the OCT optical system are converged coaxially directly under the objective lens.

Also, as a method different from the Galilean ophthalmologic microscope, there is a Greenough ophthalmologic microscope that comprises two objective lenses corresponding to the left and right observation optical systems, respectively, and sets the stereo angle between the left and right observation optical systems (Patent documents 7 and 8). In the Greenough ophthalmologic microscope, since there is no objective lens through which the optical axes of the left and right observation optical systems commonly penetrate, the light path of the OCT optical system can enter a subject's eye without penetrating through the objective lens.

However, the Greenough ophthalmologic microscope requires a complex optical design in order to incline the left and right observation optical systems each other to set the stereo angle.

While there is a Scanning Laser Ophthalmoscope (SLO) as a device for observing a subject's eye, that irradiates a laser beam to the subject's eye and detects the reflected light, a device which combines SLO and OCT has also been developed (Patent document 9).

PRIOR ART REFERENCES

Patent Documents

[Patent document 1] Japanese Unexamined Patent Application Publication No. H8-66421
[Patent document 2] Japanese Unexamined Patent Application Publication No. 2008-264488
[Patent document 3] Japanese Unexamined Patent Application Publication No. 2008-268852
[Patent document 4] Japanese Translation of PCT International Application Publication No. 2010-522055
[Patent document 5] Japanese Unexamined Patent Application Publication No. 2008-264490
[Patent document 6] U.S. Pat. No. 8,366,271
[Patent document 7] Japanese Unexamined Patent Application Publication No. 2016-185177
[Patent document 8] Japanese Unexamined Patent Application Publication No. 2016-185178
[Patent document 9] Japanese Unexamined Patent Application Publication No. 2015-221091

DISCLOSURE OF THE INVENTION

Problems to be Solved by the Invention

As described above, for the conventional ophthalmologic microscopes provided with the OCT optical system, there exist the Galilean ophthalmologic microscope and the Greenough ophthalmologic microscope, however, the latter has required a complex optical design.

Also, for the conventional Galilean ophthalmologic microscope, although many methods that the optical axis of the observation optical system and the optical axis of the OCT optical system commonly penetrate through one objective lens have been developed as indicated in Patent documents 1 to 5, etc., the degree of freedom in the optical design is limited because the OCT optical system and the observation optical system are influenced by each other as they are not independent from one another.

For the conventional Galilean ophthalmologic microscope, although the method that the optical axis of the OCT optical system does not penetrate through the objective lens has been developed as indicated in Patent document 6, there is a problem that the degree of freedom in the optical design is limited, such as being not able to secure enough distance between the ophthalmologic microscope and a subject's eye, because of the optical members of the OCT optical system provided between the objective lens and the subject's eye.

Thus, in light of the conventional situation above, the object of the present invention is to develop, for the Galilean ophthalmologic microscope provided with OCT optical system, an ophthalmologic microscope of a new method that increases the degree of freedom in the optical design.

Means for Solving the Problems

As a result of the keen research in order to solve the problems above, the inventors found that, for the Galilean ophthalmologic microscope, the observation optical system and the OCT optical system become independent from one another by placing them in such a way the optical axis of the OCT optical system does not penetrate through the objective lens through which the optical axis of the observation optical system, and the optical axis of the observation optical system and the optical axis of the OCT optical system are non-coaxial, which leads to increased degree of freedom in the optical design and also allows to detachably unitize the OCT optical system. We came to complete the present invention with findings that, due to the optical axis of the observation optical system and the optical axis of the OCT optical system being non-coaxial, a mismatch occurs between an image observed at the observation optical system and an image obtained by the OCT optical system, however, it is possible to observe a section of the subject's eye where the OCT optical system scans without a mismatch by providing a SLO optical system that guides a light ray substantially coaxial with the optical axis of the OCT optical system to the subject's eye.

That is, the present invention provides the first invention below regarding an ophthalmologic microscope, the second invention below regarding a function expansion unit, and the third invention below regarding a function expansion set.

(1) The first invention relates to an ophthalmologic microscope comprising:
an illuminating optical system for illuminating a subject's eye;
an observation optical system that comprises an observation optical system for left eye and an observation optical system for right eye to observe the subject's eye illuminated by the illuminating optical system;
an objective lens through which the optical axis of the observation optical system for left eye and the optical axis of the observation optical system for right eye of the observation optical system commonly penetrate; and
an OCT optical system for scanning a measuring light to test the subject's eye with Optical Coherence Tomography,
characterized in that the observation optical system, the objective lens, and the OCT optical system are placed in such a way that the optical axis of the OCT optical system does not penetrate through the objective lens through which the optical axis of the observation optical system penetrates, and the optical axis of the observation optical system and the optical axis of the OCT optical system are non-coaxial, and the ophthalmologic microscope further comprises a SLO optical system that scans a light ray which is a visible ray, a near infrared ray, or an infrared ray and guides the light to the subject's eye so as to become substantially coaxial with the optical axis of the OCT optical system, and it can observe a section of the subject's where the OCT optical system scans, with the SLO optical system.

(2) In the first invention, it is preferable that the OCT optical system comprises:

a first optical member that guides a light from an OCT light source to a first optical axis direction;

a first reflecting member that guides the light guided to the first optical axis direction to a second optical axis direction substantially perpendicular to the first optical axis direction;

a second optical member that relays the light guided to the second optical axis direction;

a second reflecting member that guides the light relayed by the second optical member to a third optical axis direction substantially perpendicular to the second optical axis direction; and an objective lens for OCT that is placed on the third optical axis direction and irradiates a prescribed section of the subject's eye with the light guided to the third optical axis direction.

(3) In any of ophthalmologic microscopes above, it is preferable to comprise a deflection optical element that commonly scans a measuring light of the OCT optical system and a light ray of the SLO optical system.

(4) In any of ophthalmologic microscopes above, it is preferable that the objective lens has a partial shape of circular lens or a shape of circular lens with a cutout or hole, and that the optical axis of the OCT optical system penetrates through a portion where the objective lens does not exist, or through a cutout or hole provided in the objective lens.

(5) In case of (4) above, it is possible to divide the circular lens or part of the circular lens in two, with one of the divided lenses being as the objective lens and the other being as an objective lens for OCT through which the optical axis of the OCT optical system penetrates.

(6) In any of ophthalmologic microscopes above, it is preferable to further comprise an objective lens position control mechanism that adjusts a position of the objective lens or the objective lens for OCT.

(7) In any of ophthalmologic microscopes above, it is preferable that the OCT optical system and the SLO optical system are detachably unitized.

(8) In any of ophthalmologic microscopes above, it is preferable to further comprise a detachable front-end lens onto a light path between the subject's eye and the objective lens to observe a retina of the subject's eye.

(9) The second invention relates to a function expansion unit used for an ophthalmologic microscope comprising: an illuminating optical system for illuminating a subject's eye, an observation optical system that comprises an observation optical system for left eye and an observation optical system for right eye to observe the subject's eye illuminated by the illuminating optical system, and an objective lens through which the optical axis of the observation optical system for left eye and the optical axis of the observation optical system for right eye of the observation optical system commonly penetrate, characterized in that the function expansion unit comprises:

a joint detachable against the ophthalmologic microscope;

an OCT optical system for scanning a measuring light to test the subject's eye with Optical Coherence Tomography; and a SLO optical system that scans a light ray which is a visible ray, a near infrared ray, or an infrared ray and guides the light to the subject's eye;

wherein the optical axis of the OCT optical system does not penetrate through the objective lens through which the optical axis of the observation optical system penetrates, and the optical axis of the observation optical system and the optical axis of the OCT optical system are non-coaxial, when the function expansion unit is attached to the ophthalmologic microscope via the joint, and wherein the optical axis of the OCT optical system and the optical axis of the SLO optical system are substantially coaxial, and the ophthalmologic microscope can observe a section of the subject's where the OCT optical system scans, with the SLO optical system.

(10) In the function expansion unit of the second invention, it is preferable that the OCT optical system comprises:

a first optical member that guides a light from an OCT light source to a first optical axis direction;

a first reflecting member that guides the light guided to the first optical axis direction to a second optical axis direction substantially perpendicular to the first optical axis direction;

a second optical member that relays the light guided to the second optical axis direction;

a second reflecting member that guides the light relayed by the second optical member to a third optical axis direction substantially perpendicular to the second optical axis direction; and an objective lens for OCT that is placed on the third optical axis direction and irradiates a prescribed section of the subject's eye with the light guided to the third optical axis direction.

(11) In any of function expansion units above, it is preferable to comprise a deflection optical element that commonly scans a measuring light of the OCT optical system and a light ray of the SLO optical system.

(12) The third invention provides a function expansion set characterized in that it comprises any of function expansion units above and an objective lens for replacement to replace the objective lens.

(13) In the third invention, it is preferable that the objective lens for replacement has a partial shape of circular lens or a shape of circular lens with a cutout or hole, and that when replacing the objective lens with the objective lens for replacement and attaching the function expansion unit to the ophthalmologic microscope via the joint, the optical axis of the OCT optical system penetrates through a portion where the objective lens for replacement does not exist, or through a cutout or hole provided in the objective lens for replacement.

Effect of the Invention

In the ophthalmologic microscope of the first invention, the optical axis of the OCT optical system does not penetrate the objective lens through, and the optical axis of the observation optical system and the optical axis of the OCT optical system are non-coaxial. With this configuration, the ophthalmologic microscope of the present invention is one which the observation optical system and the OCT optical system are independent from one another. Therefore, in the ophthalmologic microscope of the present invention, as it is possible to perform optical design without the observation optical system and the OCT optical system being influenced each other, the ophthalmologic microscope of the present invention is effective in increasing the degree of freedom in the optical design. Also, the ophthalmologic microscope of the present invention comprises a SLO optical system that guides a light ray substantially coaxial with the optical axis of the OCT optical system to a subject's eye, thereby is effective in observing the subject's eye without a mismatch from an image obtained by the OCT optical system.

For the function expansion unit of the second invention and the function expansion set of the third invention, the optical axis of the OCT optical system for the function expansion unit does not penetrate the objective lens through which the optical axis of the observation optical system for the ophthalmologic microscope penetrates, and the optical axis of the observation optical system for the ophthalmologic microscope and the optical axis of the OCT optical system for the function expansion unit are non-coaxial. With this configuration, the OCT optical system for the function expansion unit is independent from the observation optical system for the ophthalmologic microscope, thereby allows for unitization and is effective in increasing the degree of freedom in the optical design. As the function expansion unit is detachable to the ophthalmologic microscope via a joint, the function expansion unit and the function expansion set of the present invention are effective in readily adding functions of OCT to the ophthalmologic microscope. Also, the function expansion unit and the function expansion set of the present invention comprise a SLO optical system that guides a light ray substantially coaxial with the optical axis of the OCT optical system to a subject's eye, thereby are effective in observing the subject's eye without a mismatch from an image obtained by the OCT optical system.

BRIEF DESCRIPTION OF THE DRAWINGS

FIG. 5 (A) is a view from the direction of the optical axis of the objective lens and FIG. 5 (B) is a cross-sectional view along the plane including the line AA' of FIG. 5 (A).

FIG. 12 (A) illustrates an objective lens seen from the optical axis direction and FIG. 12 (B) is a cross-sectional view of FIG. 12 (A) in the plane including a line AA'.

FIG. 13 (A) is a view from the direction of the optical axis of the objective lens and FIG. 13 (B) is a cross-sectional view of FIG. 13 (A) in the plane including a line AA'.

FIG. 14 schematically illustrates a shape of objective lens used for the ophthalmologic microscope of the fifth embodiment of the present invention. FIG. 14 (A) is a view from the direction of the optical axis of the objective lens and FIG. 14(B) is a cross-sectional view FIG. 14 (A) in the plane including a line AA'.

FIG. 15 (A) is a view from the direction of the optical axis of the objective lens and FIG. 15 (B) is a cross-sectional view of FIG. 15 (A) in the plane including a line AA'.

FIG. 16 (A) is a view from the direction of the optical axis of the objective lens and FIG. 16 (B) is a cross-sectional view of FIG. 16(A) in the plane including a line AA'.

DESCRIPTION OF EMBODIMENTS

Figure 1:
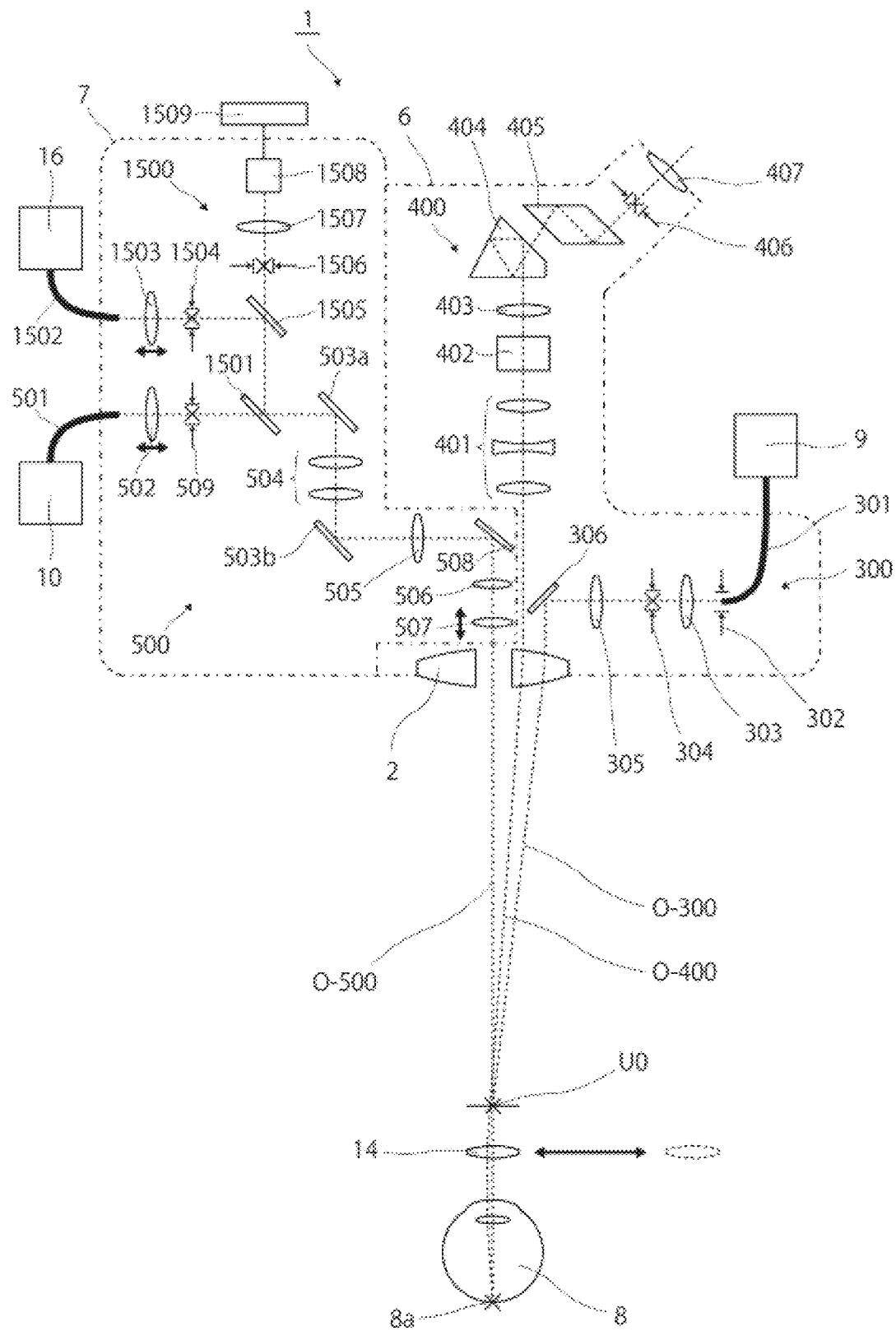
FIG. 1 schematically illustrates the configuration of an optical system taken from a side view, regarding to the ophthalmologic microscope of the first embodiment of the present invention.

1. Ophthalmologic Microscope 1-1. Summary of the Ophthalmologic Microscope of the Present Invention The ophthalmologic microscope of the present invention relates to an ophthalmologic microscope comprising: an illuminating optical system for illuminating a subject's eye; an observation optical system that comprises an observation optical system for left eye and an observation optical system for right eye to observe the subject's eye illuminated by the illuminating optical system; an objective lens through which the optical axis of the observation optical system for left eye and the optical axis of the observation optical system for right eye of the observation optical system commonly penetrate, and an OCT optical system for scanning a measuring light to test the subject's eye with Optical Coherence Tomography.

For the ophthalmologic microscope of the present invention, the observation optical system, the objective lens, and the OCT optical system are placed in such a way that the optical axis of the OCT optical system does not penetrate through the objective lens through which the optical axis of the observation optical system penetrates, and the optical axis of the observation optical system and the optical axis of the OCT optical system are non-coaxial. With this configuration, the ophthalmologic microscope of the present invention is one which the observation optical system and the OCT optical system are independent from one another.

Therefore, in the ophthalmologic microscope of the present invention, as it is possible to perform optical design without the observation optical system and the OCT optical system being not influenced each other, the ophthalmologic microscope of the present invention is effective in increasing the degree of freedom in the optical design.

For example, but not limited to, providing an OCT optical system with an objective lens for OCT in addition to an objective lens of the observation optical system and controlling the position of the respective objective lenses independently allow for an optical design that adjusts the focus of the observation optical system and the focus of the OCT optical system independently. It also allows for an optical design that separates the OCT optical system from the observation optical system to make the OCT optical system a detachable unit to the ophthalmologic microscope. Furthermore, it allows for an optical design that can obtain 3D tomographic images in more detail by adding not only one but also a plurality of OCT optical systems to the ophthalmologic microscope.

Thus, as the optical axis of the observation optical system and the optical axis of the OCT optical system are non-coaxial, the center of an image observed by the observation optical system (the portion overlapped with the optical axis of the observation optical system) and the center of an image obtained by the OCT optical system (the portion overlapped with the optical axis of the OCT optical system) does not match and thus a mismatch occurs between both images. Therefore, it becomes difficult to accurately align the image observed by the observation optical system and the image obtained by the OCT optical system.

However, the ophthalmologic microscope of the present invention further comprises a SLO optical system that scans a light ray which is a visible ray, a near infrared ray, or an infrared ray and guides the light to the subject's eye so as to become substantially coaxial with the optical axis of the OCT optical system. This SLO optical system allows to observe the subject's eye without any mismatch from an image obtained by OCT optical system. For example, by imaging the shape of fundus surface with the SLO optical system and displaying it on a part of the displaying portion (display), meanwhile making that image correspond to a tomographic image obtained by the OCT optical system and superimposing or displaying the tomographic image on other part of the displaying portion, it is possible for an observer to know exactly to which section of the fundus surface the tomographic image corresponds.

In the present invention, "ophthalmologic microscope" refers to a medical or inspection equipment that can enlarge a subject's eye to observe, and it encompasses one not only for human but also for animal. "Ophthalmologic microscope" includes, for example, but not limited to, a fundus camera, a slit lamp, a microscope for ophthalmic surgery, etc.

In the present invention, "illuminating optical system" is configured to include an optical element for illuminating a subject's eye. The illuminating optical system may further include a light source, but it may guide natural light to a subject's eye.

Also, in the present invention, "observation optical system" is configured to include an optical element that can observe a subject's eye with return light which is reflected/scattered from the subject's eye illuminated by the illuminating optical system. In the present invention, the observation optical system comprises an observation optical system for left eye and an observation optical system for right eye, so it is possible to observe stereoscopically with binocular vision when generating a parallax in the image obtained by the left and right observation optical systems.

Also, "observation optical system" of the present invention may directly observe a subject's eye through an eyepiece lens, etc., may observe it by accepting a light with an imaging element, etc., for imaging, or may be provided with both functions.

In the present invention, "OCT optical system" is configured to include an optical element that the measuring light of OCT passes through. The OCT optical system may further include an OCT light source.

In the present invention, as an optical element used in "illuminating optical system", "observation optical system", "OCT optical system", for example, but not limited to, a lens, a prism, a mirror, a light filter, a diaphragm, a diffraction grating, a polarizing element, etc. can be used.

In the present invention, "objective lens" is a lens in the ophthalmologic microscope, which is provided at the side of a subject's eye. "Objective lens" of the present invention does not include a front-end lens (loupe) inserted between an objective lens and a subject's eye to use.

In the present invention, the optical axis of the observation optical system and the optical axis of the OCT optical system "are non-coaxial" means that directions of the optical axis of the observation optical system and the optical axis of the OCT optical system are not identical in the region between the objective lens of the ophthalmologic microscope and the subject's eye.

Although "objective lens" in the present invention is an objective lens through which the optical axis of the observation optical system for left eye and the optical axis of the observation optical system for right eye commonly penetrate, the optical axis of the OCT optical system does not penetrate through the objective lens as mentioned above. Also, the optical axis of the illuminating optical system may or may not penetrate through the objective lens. An additional objective lens for illuminating can be provided when the optical axis of the illuminating optical system does not penetrate through the objective lens.

"A light ray which is a visible ray, a near infrared ray, or an infrared ray" used in the SLO optical system of the ophthalmologic microscope of the present invention may be any kind of light ray including wave length in the visible area, near infrared area, or infrared area, but preferably a highly directional light ray. More preferably, a laser beam may be used.

Also, the SLO optical system "becomes substantially coaxial" with the optical axis of the OCT optical system means that the directions of the each optical axis may be approximately identical in the main region between the objective lens of the ophthalmologic microscope and the subject's eye and thus there may be a small mismatch. Here, although the direction of light waves since the light path of the OCT optical system and the light path of the SLO optical system are both being scanned, the optical axes of the optical systems in the center of the light paths may be approximately coaxial. Even if there is a small mismatch between the directions of the optical axes, it may be less than 6°, more preferably less than 4°, yet more preferably less than 1°.

Although the ophthalmologic microscope of the present invention comprises an OCT optical system and a SLO optical system, it is preferable to have a part of the OCT optical system and the SLO optical system as a shared optical system from a perspective of downsizing the device. In particular, it is preferred to share a deflection optical element that scans a measuring light of the OCT optical system and a light ray of the SLO optical system.

When sharing a part of the optical systems, it is preferred to make the optical axis of the OCT optical system and the optical axis of the SLO optical system substantially coaxial at the side of a subject's eye and to separate a measuring light of the OCT optical system and a light ray of the SLO optical system at the side of a detecting system. In this case, for the separation of the measuring light and the light ray, for example, characteristics such as the wavelength and deflection of the light can be used to separate with a dichroic mirror and an optical filter, etc.

Because the scan range of the OCT optical system and the scan range of the SLO optical system are identical when converging a measuring light of the OCT optical system and a light ray of the SLO optical system, and then scanning them with the same deflection optical element, the alignment of the both images becomes easier.

The deflection optical element that the OCT optical system and the SLO optical system share may be any optical element that can change the direction of light and scan the light. For example, but not limited to, an optical element comprising a reflection portion that its orientation changes, like a galvano mirror, a polygon mirror, a rotation mirror, a MEMS (Micro Electro Mechanical Systems) mirror, etc., and an optical element that can changes the direction of light with an electric field or acoustic-optic effects, like a deflection prism scanner and AO element, can be employed.

1-2. First Embodiment

Hereinafter, examples of the embodiments of the present invention will be fully described in reference to drawings.

Figure 2:
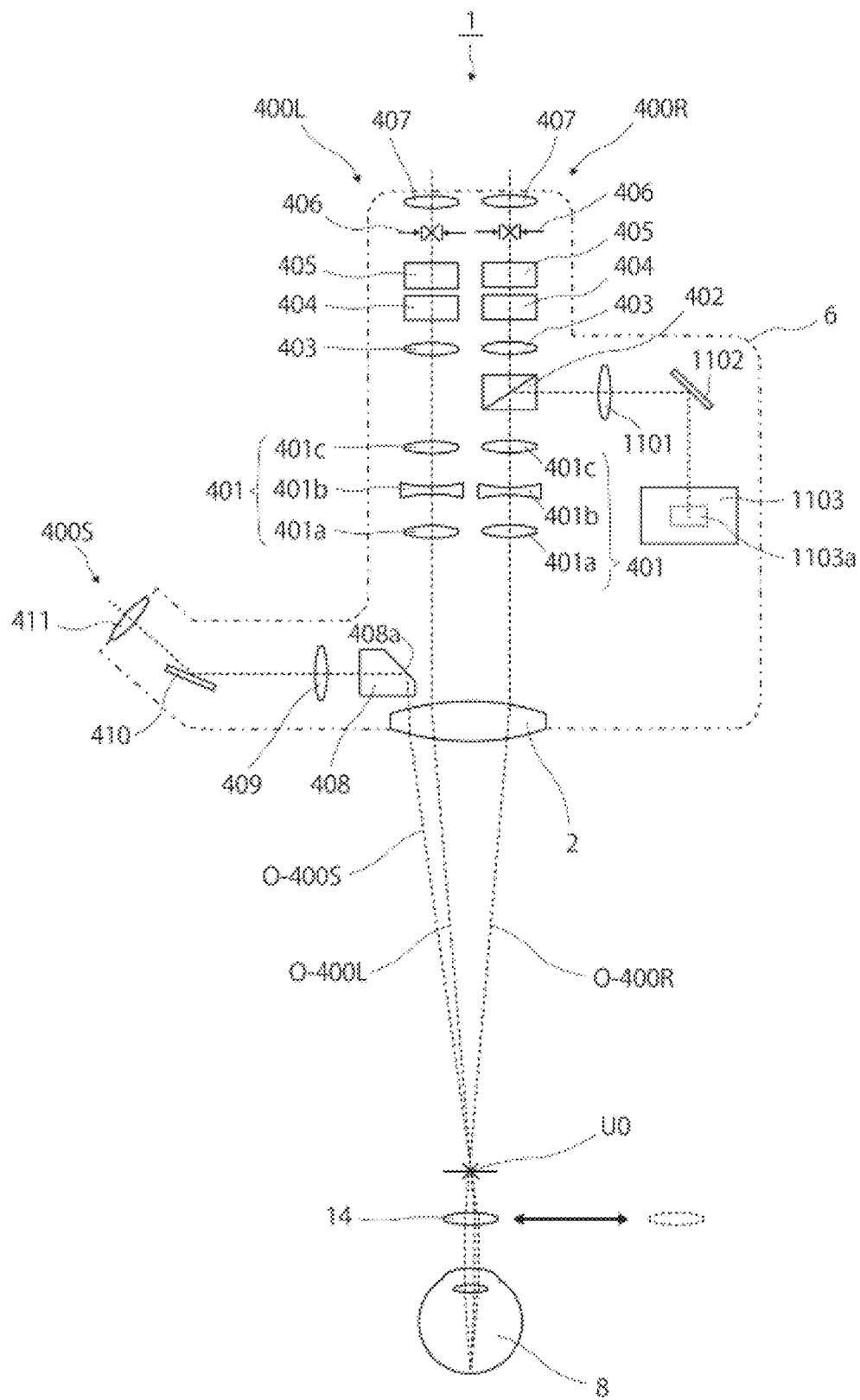
FIG. 2 schematically illustrates the configuration of an optical system taken from a front view, regarding to the ophthalmologic microscope of the first embodiment of the present invention.
Figure 3:
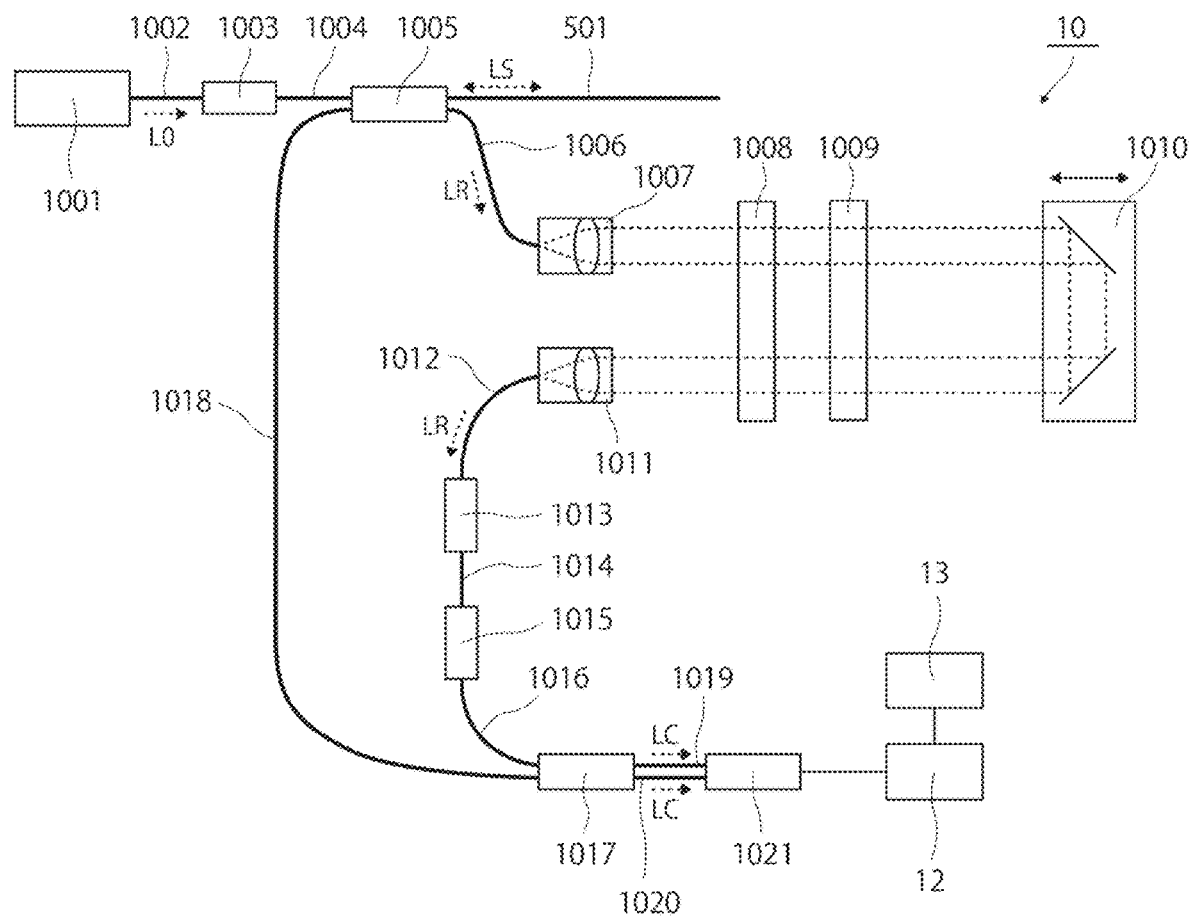
FIG. 3 schematically illustrates the optical configuration of an OCT unit used in the ophthalmologic microscope of the first embodiment of the present invention.
Figure 4:
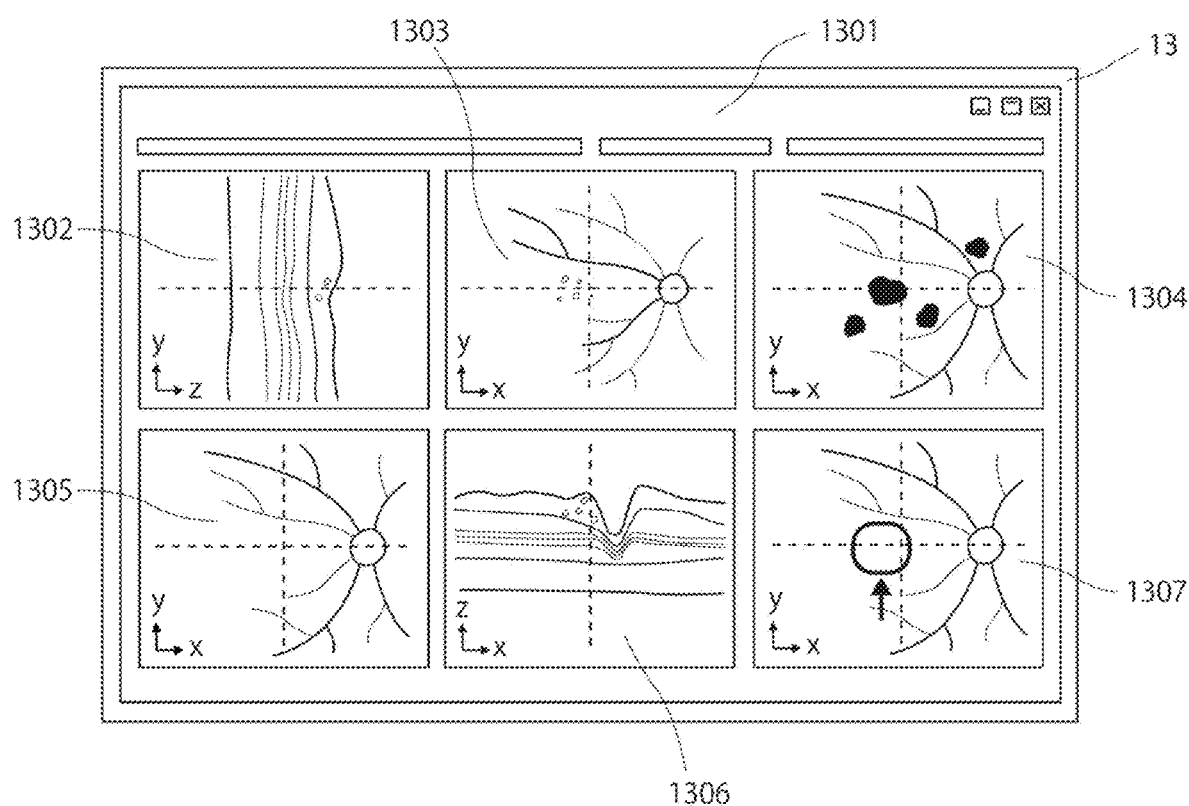
FIG. 4 schematically illustrates a displaying portion for displaying the obtained OCT images and SLO images on the ophthalmologic microscope of the first embodiment.
Figure 5A:
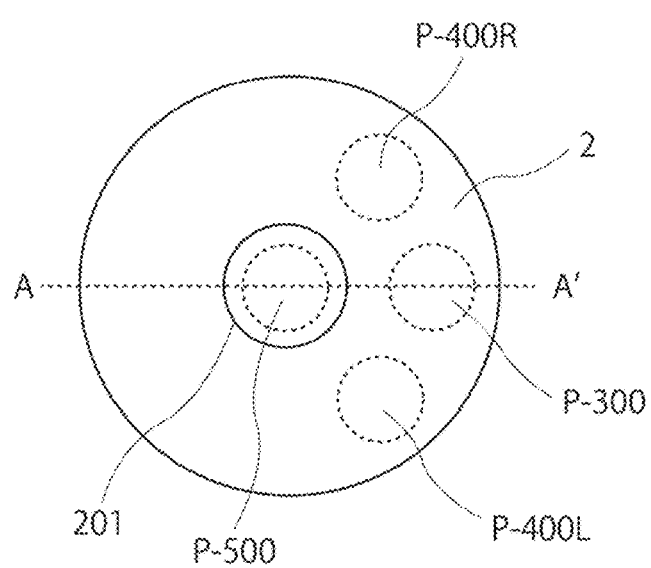
FIG. 5 schematically illustrates shapes of an objective lens used for the ophthalmologic microscope of the first embodiment of the present invention.
Figure 5B:
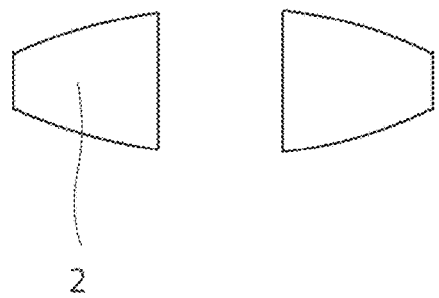

FIGS. 1-4 schematically illustrate the first embodiment which is an example of the ophthalmologic microscope of the present invention. FIG. 1 is a schematic diagram from a side view of the configuration of an optical system for the ophthalmologic microscope of the first embodiment, and FIG. 2 is a schematic diagram from a front view. Also, FIG. 3 schematically illustrates the optical configuration of an OCT unit, FIG. 4 is a schematic diagram of a displaying portion for displaying obtained OCT images and SLO images, and FIG. 5 schematically illustrates a shape of objective lens.

As shown in FIG. 1, the optical system of the ophthalmologic microscope 1 comprises an objective lens 2, an illuminating optical system 300, an observation optical system 400, an OCT optical system 500, and a SLO optical system 1500.

The objective lens 2, the illuminating optical system 300, and the observation optical system 400 are accommodated in an ophthalmologic microscope body 6. On the other hand, the OCT optical system 500 and the SLO optical system 1500 are accommodated in a function expansion unit 7. In FIG. 1, the ophthalmologic microscope body 6 and the function expansion unit 7 are respectively indicated by dashed-dotted lines.

The ophthalmologic microscope body 6 and the function expansion unit 7 are detachably coupled by a joint (not shown).

As shown in FIG. 1, the illuminating optical system 300 illuminates a subject's eye 8 through the objective lens 2. The illuminating optical system 300 is configured to include an illuminating light source 9, an optical fiber 301, an emission opening diaphragm 302, a condenser lens 303, an illuminating field diaphragm 304, a collimating lens 305, and a reflecting mirror 306. The optical axis of the illuminating optical system 300 is indicated by a dotted line O-300 in FIG. 1.

The illuminating light source 9 is provided outside of the ophthalmologic microscope body 6. The illuminating light source 9 is connected to one end of the optical fiber 301. The other end of the optical fiber is placed at the position facing the condenser lens 303 the inside of the ophthalmologic microscope body 6. The illuminating light output from the illuminating light source 9 is guided by the optical fiber 301 to enter the condenser lens 303.

The emission opening diaphragm 302 is provided at the position facing the emission opening of the optical fiber 301 (a fiber end at the condenser lens 303). The emission opening diaphragm 302 functions so as to block a partial region of the emission opening of the optical fiber 301. Once the region blocked by the emission opening diaphragm 302 is changed, the emission region of the illuminating light is changed. Thereby, the irradiation angle of the illuminating light, that is, an angle between the incident direction of the illuminating light against the subject's eye 8 and the optical axis of the objective lens 2 can be changed.

The illuminating field diaphragm 304 is provided at the position optically conjugate to the front side focal position U0 of the objective lens 2 (the position of X). The collimating lens 305 converts the illuminating light that passed through the illuminating field diaphragm 304 into a parallel light flux. The reflecting mirror 306 reflects the illuminating light converted into a parallel light flux by the collimating lens 305, towards the objective lens 2. The reflected light is irradiated towards the subject's eye 8 through the objective lens 2.

(A part of) the illuminating light irradiated towards the subject's eye 8 is reflected/scattered at the tissue of the subject's eye, such as a cornea and retina. That reflected/scattered return light (also referred as "observed light") penetrates through the objective lens 2 and enters the observation optical system 400.

As shown in FIG. 1, the observation optical system 400 is configured to include a variable magnification lens system 401, a beam splitter 402, an imaging lens 403, an image erecting prism 404, an eye width adjusting prism 405, a field diaphragm 406, and an eyepiece lens 407. The optical axis of the observation optical system 400 is indicated by a dotted line O-400 in FIG. 1.

The observation optical system 400 is used to observe the subject's eye 8, which is being illuminated by the illuminating optical system 300, via the objective lens 2.

As shown in FIG. 1, the OCT optical system 500 is configured to include an OCT unit 10, an optical fiber 501, a collimating lens 502, an illuminating field diaphragm 509, a dichroic mirror 1501, optical scanners 503a, 503b, a relay optical system 504, a first lens group 505, a reflecting mirror 508, a second lens group 506, and an objective lens for OCT 507.

The optical axis of the OCT optical system 500 is indicated by a dotted line O-500 in FIG. 1.

As shown in FIG. 1, in the first embodiment, the optical axis of the OCT optical system O-500 does not penetrate through the objective lens 2, the optical axis of the observation optical system O-400 and the optical axis of the OCT optical system O-500 are non-coaxial, and thus the OCT optical system and the observation optical system are independent from one another.

The OCT unit 10 divides the light from a low coherence (short coherence length) OCT light source into a measuring light and a reference light. The measuring light is guided by the OCT optical system 500 and irradiated towards the subject's eye 8, then it reflects/scatters at the tissue of the subject's eye and becomes a return light to be guided to the OCT unit 10. The interference between the return light and the reference light of the measuring light is detected at the OCT unit 10. This allows to obtain tomographic images of the tissue of the subject's eye.

As shown in FIG. 1, the OCT unit 10 is provided outside of the function expansion unit 7 but coupled with it by being connected to the one end of the optical fiber 501. The measuring light generated by the OCT unit 10 emits from the other end of the optical fiber 501. The emitted measuring light is irradiated towards the subject's eye 8 by way of the collimating lens 502, the illuminating field diaphragm 509, the dichroic mirror 1501, the optical scanners 503*a*, 503*b*, the relay optical system 504, the first lens group 505, the reflecting mirror 508, the second lens group 506, the objective lens for OCT 507, etc., and the return light of the measuring light reflected/scattered at the tissue of the subject's eye 8 travels the same pathway in opposite direction and enters the other end of the optical fiber 501.

When observing a retina at the fundus of the eye, the front-end lens 14 is inserted onto optical axes O-300, O-400, O-500 right in front of the subject's eye by a moving means (not shown). In this case, the front side focal position U0 of the objective lens 2 is conjugate to the retina 8*a* at the fundus of eye.

Also, when observing an anterior eye part such as a cornea, an iris, etc., the observation is performed by eliminating the front-end lens from right in front of the subject's eye and aligning the front side focal position U0 with the anterior eye part.

As shown in FIG. 1, the collimating lens 502 converts the measuring light emitted from the other end of the optical fiber 501 into a parallel light flux. The collimating lens 502 and the other end of the optical fiber 501 are configured to be relatively movable along the optical axis of the measuring light. In the first embodiment, the collimating lens 502 is configured to be movable, while the other end of the optical fiber 501 may be configured to be movable along the optical axis of the measuring light.

The illuminating field diaphragm 509 is conjugate to the front side focal position U0 of the objective lens 2. The dichroic mirror 1501 is configured with a reflecting member that transmits the measuring light of the OCT optical system 500 without reflecting it.

The optical scanners 503*a*, 503*b* in the OCT optical system are deflection optical elements that two-dimensionally deflect the measuring light converted into a parallel light flux by the collimating lens 502. The optical scanner is a galvano mirror that includes a first scanner 503*a* comprising a deflection plane rotatable around a first axis and a second scanner 503*b* comprising a deflection plane rotatable around a second axis orthogonal to the first axis. The relay optical system 504 is provided between the first scanner 503*a* and the second scanner 503*b*. The relay optical system 504 may not be provided, if the distance between the first scanner 503*a* and the second scanner 503*b* is shortened, etc.

The first lens group 505 is configured to include one or more lenses. The second lens group 506 also configured to include one or more lenses. The reflecting mirror 508 located between the first lens group 505 and the second lens group 506 changes the direction of light towards the subject's eye 8.

Moreover, the objective lens for OCT 507 is provided on the side having contact with the subject's eye 8.

The objective lens for OCT is configured to be movable along the optical axis, so it is possible to adjust the focus of the OCT optical system by controlling the position of the objective lens for OCT. This allows to adjust the focus of the OCT optical system to the position different from the focus of the observation optical system.

Thus, in the ophthalmologic microscope of the first embodiment, since the optical axis of the OCT optical system O-500 does not penetrate through the objective lens 2, and the optical axis of the observation optical system O-400 and the optical axis of the OCT optical system O-500 are non-coaxial, the observation optical system and the OCT optical system are independent from one another.

Therefore, in the ophthalmologic microscope of the first embodiment, it is possible to control the observation optical system and the OCT optical system independently, and it is also possible to have the OCT optical system as a unit detachable to the ophthalmologic microscope.

As shown in FIG. 1, the ophthalmologic microscope 1 of the present invention further comprises a SLO optical system 1500. The SLO optical system 1500 is configured to include a SLO light source 16, an optical fiber 1502, a collimating lens 1503, an illuminating field diaphragm 1504, a dichroic mirror 1501, a half mirror 1505, an optical diaphragm 1506, a condensing lens 1507, a reflected light detector 1508, and an image generation part 1509.

The SLO light source 16 is provided outside of the function expansion unit 7 but coupled with it by being connected to the one end of the optical fiber 1502. The light ray generated by the SLO light source 16 emits from the other end of the optical fiber 1502. The emitted light ray is reflected at the half mirror 1505 through the collimating lens 1503, the illuminating field diaphragm 1504, and also reflected at the dichroic mirror 1501 to converge coaxially to the measuring light of the OCT optical system 500.

As shown in FIG. 1, the converged light ray of the SLO optical system 1500 is two-dimensionally scanned at the optical scanners 503*a*, 503*b* same as the measuring light of the OCT optical system 500. The function expansion unit 7 can be downsized/produced at a lower cost by commonly using the optical scanners 503*a*, 503*b* that require a complex mechanism, at the OCT optical system 500 and the SLO optical system 1500.

In the ophthalmologic microscope of the present invention, it is also possible to scan the OCT optical system and the SLO optical system independently by providing separate optical scanners for the OCT optical system and the SLO optical system respectively. This allows to simultaneously scan different sites of an observed plane.

The light ray of the SLO optical system 1500 scanned at the optical scanners 503*a*, 503*b* is irradiated towards the subject's eye 8 by way of the relay optical system 504, the first lens group 505, the reflecting mirror 508, the second lens group 506, the objective lens for OCT 507, etc. Here, the optical axis of the SLO optical system O-500 guided to the subject's eye 8 is coaxial with the optical axis of the OCT optical system O-500. And the return light of the light ray reflected/scattered at the tissue of the subject's eye 8 travels the same pathway in opposite direction, and it is reflected at the dichroic mirror 1501, and detected at the reflected light detector 1508 after penetrating through the half mirror 1505 by way of the optical diaphragm 1506, the condensing lens 1507. The detected signal is exchanged with an image by the image generation part 1509.

As shown in FIG. 1, the dichroic mirror 1501 transmits the measuring light of the OCT optical system 500 and reflects the light ray of the SLO optical system 1500. This allows to converge/separate the measuring light of the OCT optical system 500 and the light ray of the SLO optical system 1500.

The half mirror 1505 reflects some of the light ray of the SLO optical system 1500 and transmits some. The half mirror 1505 allows to separate the light source side and the light reception side of the SLO optical system 1500.

The optical diaphragm 1506 is conjugate to the front side focal position U0 of the objective lens 2, and the condensing lens 1507 concentrates the light ray reflected/scattered at the subject's eye 8.

The reflected light detector 1508 comprises a light detection element that detects a weak light ray reflected/scattered at the subject's eye 8, and it is configured with an APD (avalanche photodiode) or a photo multiplier tube, for example. The detected signal from the reflected light detector 1508 is sent to the image generation part 1509. The scanned data of the subject's eye 8 is obtained by irradiating the light ray from the SLO light source 16 towards the subject's eye 8 while scanning it with the optical scanners 503a, 503b, and detecting the light ray reflected/scanned at the subject's eye 8 with the reflected light detector 1508. The image generation part 1509 generate an image of the subject's eye 8 based on this scanned data. This image is sent to the display and displayed, and this allows to observe the form of the tissue of the subject's eye.

Based on the signal and image obtained by the SLO, it is possible to track the movement of a subject's site during OCT scanning. Although a mismatch occurs in a tomographic image obtained by the OCT if the subject's eye moves during OCT scanning due to an involuntary eye movement of the subject's eye, surgery operation, etc., it is possible to obtain tomographic images of the OCT without a mismatch by detecting the movement of the fundus based on the signal and image obtained by the SLO and scanning the OCT optical system in accordance with this movement.

The ophthalmologic microscope of the first embodiment further will be further fully described in reference to drawings.

FIG. 2 is a schematic diagram from a front view of the configuration of an optical system for the ophthalmologic microscope of the first embodiment.

As shown in FIG. 2, the observation optical system is separated into observation optical systems for left eye 400L and for right eye 400R of an observer, each comprising an observation light path. The optical axes of the left and right observation optical systems are indicated by dotted lines O-400L, O-400R, respectively, in FIG. 2.

As shown in FIG. 2, the left and right observation optical systems 400L, 400R are each configured to include a variable magnification lens system 401, an imaging lens 403, an image erecting prism 404, an eye width adjusting prism 405, a field diaphragm 406, and an eyepiece lens 407. Only the observation optical system for right eye 400R comprises a beam splitter 402.

The variable magnification lens system 401 is configured to include a plurality of zoom lenses 401a, 401b, 401c. Each zoom lens 401a, 401b, 401c is movable along the optical axes of the left and right observation optical systems O-400L, O-400R with a variable power mechanism (not shown). This alters the magnification in observing or imaging the subject's eye 8.

As shown in FIG. 2, the beam splitter 402 of the observation optical system for right eye 400R separates some of the observed light guided from the subject's eye 8 along the observation optical system for right and guides it towards the imaging optical system. The imaging optical system is configured to include an imaging lens 1101, a reflecting mirror 1102, and a television camera 1103.

The television camera 1103 is provided with an imaging element 1103a. The imaging element 1103a is configured with, for example, a CCD (Charge Coupled Devices) image sensor, a CMOS (Complementary Metal Oxide Semiconductor) image sensor, etc. As an imaging element 1103a, one comprising a two-dimensional light reception plane (area sensor) is used.

The light reception plane of the imaging element 1103a is placed at the position optically conjugate to the front side focal position U0 of the objective lens 2.

The beam splitter and the imaging optical system may exist in the both right and left observation optical systems. It is possible to obtain a stereoscopic image by retrieving images having parallax at respective right and left imaging elements.

Camera images can be used for obtaining an image of observation sites and also for tracking OCT observation sites based on the obtained signals and images. It is possible to correct a mismatch due to an involuntary eye movement of the subject's eye during scanning with OCT, surgery operation, etc.

The image erecting prism 404 converts an inverted image to an erecting image. The eye width adjusting prism 405 is an optical element for adjusting the distance between right and left light paths depending on the eye width of an observer (distance between a left eye and a right eye). The field diaphragm 406 blocks a peripheral region in the cross section of the observed light to restrict the observer's field of view. The field diaphragm 406 is provided at the position conjugate to the front side focal position U0 of the objective lens 2 (the position of X).

The observation optical systems 400L, 400R may be configured to include a stereo variator configured to be removal from the light path of the observation optical system. The stereo variator is an optical axis position altering element for altering the relative position of the axes of the left and right optical observation optical systems O-400L, O-400R led respectively by the right and left variable magnification lens systems 401. The stereo variator is, for example, evacuated to the evacuation position provided on the observer side for the observed light path.

In the ophthalmologic microscope of the first embodiment, a sub-observation optical system 400S for an assistance observer to use is provided in addition to the observation optical system for a main observer to use.

As shown in FIG. 2, the sub-observation optical system 400S guides the return light (observed light) reflected/scattered at the subject's eye 8 which is being illuminated with the illuminating optical system, towards the eyepiece lens for assistant 411 by way of the objective lens 2. The optical axis of the sub-observation optical system is indicated by a dotted line O-400S in FIG. 2.

The sub-observation optical system 400S is also provided with a pair of right and left optical systems and capable of stereoscopic observation with the binocular.

As shown in FIG. 2, the sub-observation optical system 400S is configured to include a prism 408, a reflecting mirror 410, and an eyepiece lens for assistant 411. In the first embodiment, an imaging lens 409 is also placed between the prism 408 and the reflecting mirror 410. The observed light from the subject's eye 8 penetrates through the objective lens 2 and it is reflected by the reflecting surface 408a of the prism 408. The observed light reflected by the reflecting surface 408a penetrates through the imaging lens 409 and it is reflected by the reflecting mirror 410 and guided to the eyepiece lens for assistant 411.

The observation optical systems 400L, 400R and the sub-observation optical system 400S are accommodated in the ophthalmologic microscope body 6.

When observing a retina at the fundus of the eye, the front-end lens 14 is inserted onto optical axes O-400L, O-400R, O-400S right in front of the subject's eye by a moving means (not shown). In this case, the front side focal position U0 of the objective lens 2 is conjugate to the retina 8a at the fundus of eye.

Also, when observing an anterior eye part such as a cornea, an iris, etc., the observation is performed by eliminating the front-end lens from right in front of the subject's eye and aligning the front side focal position U0 with the anterior eye part.

FIG. 3 schematically illustrates the optical configuration of the OCT unit 10 used in the ophthalmologic microscope of the first embodiment.

In addition to the Fourier domain type illustrated below, the OCT may be other type of OCT, including a spectral domain type.

As shown in FIG. 3, the OCT unit 10 constitutes an interferometer that divides the light emitted from the OCT light source unit 1001 into the measuring light LS and the reference light LR and detects interference between the measuring light LS and the reference light LR went through different light paths.

The OCT light source unit 1001 is configured to include a wavelength scanning (wavelength sweeping) light source capable of scanning (sweeping) the wavelength of the emitted light, similar to the general OCT device of the swept source type. The OCT light source unit 1001 changes the output wavelength temporally for the near infrared wavelength which is unrecognizable by human eyes. The light output from the OCT light source unit 1001 is indicated by a symbol L0.

The light L0 output from the OCT light source unit 1001 is guided to the polarized wave controller 1003 by the optical fiber 1002 and adjusted its polarizing condition. The polarized wave controller 1003 adjusts the polarizing condition of the light L0 guided within the optical fiber 1002 by applying stress to, for example, the loop-shaped optical fiber 1002, from outside.

The light L0 whose polarizing condition has been adjusted by the polarized wave controller 1003 is guided to the fiber coupler 1005 by the optical fiber 1004 and divided into the measuring light LS and the reference light LR.

As shown in FIG. 3, the reference light LR is guided by an optical fiber 1006 to a collimator 1007 and converted into a parallel light flux. The reference light LR which became a parallel light flux is guided to a corner cube 1010 by way of a light path length correction member 1008 and a dispersion compensation member 1009. The light path length correction member 1008 functions as a delay mean for matching the light path lengths (optical distance) of the reference light LR and the measuring light LS. The dispersion compensation member 1009 functions as a dispersion compensation mean for matching the dispersion characteristics (optical distance) of the reference light LR and the measuring light LS.

The corner cube 1010 turns the reference light LR which was converted into a parallel light flux by the collimator 1007, from the advancing direction to the opposite direction. The light path of the reference light LR incident on the corner cube 1010 and the light path of the reference light LR emitted from the corner cube 1010 are parallel. Also, the corner cube 1010 will be movable to the direction along the incident light path and the emitting light path of the reference light LR. This movement alters the length of the light path of the reference light LR (reference light path).

As shown in FIG. 3, the reference light LR through the corner cube 1010 goes through the dispersion compensation member 1009 and the light path length correction member 1008, enters the optical fiber 1012 after it is converted from a parallel light flux to a focused light flux by the collimator 1011, and it is guided to the polarized wave controller 1013 and adjusted its polarizing condition.

The polarized wave controller 1013 has a similar configuration to the polarized wave controller 1003, for example. The reference light LR whose polarizing condition has been adjusted by the polarized wave controller 1013 is guided to an attenuator 1015 by an optical fiber 1014 and adjusted its light volume under control of an arithmetic control unit 12. The reference light LR whose light volume has been adjusted by the attenuator 1015 is guided to a fiber coupler 1017 by an optical fiber 1016.

As seen from FIGS. 1 and 3, the measuring light LS generated by the fiber coupler 1005 is guided to the collimating lens 502 by the optical fiber 501. As shown in FIG. 1, the measuring light incident on the collimating lens 502 is irradiated towards the subject's eye 8 by way of the illuminating field diaphragm 509, the optical scanners 503a, 503b, the relay optical system 504, the first lens group 505, the reflecting mirror 508, the second lens group 506, and the objective lens for OCT 507. The measuring light is reflected/scattered at various depth positions of the subject's eye 8. The measuring light backscattered from the subject's eye 8 travels backwards the same pathway as the forward route and it is guided by the fiber coupler 1005 to reach the fiber coupler 1017 by way of the optical fiber 1018, as shown in FIG. 3.

The fiber coupler 1017 synthesizes (causes the interference between) the measuring light LS incident through the optical fiber 1018 and the reference light LR incident through the optical fiber 1016 to generate an interfering light. The fiber coupler 1017 generates a pair of interfering lights LC by branching the interfering light of the measuring light LS and the reference light LR at a predetermined branching ratio (for example, 50:50). The pair of interfering lights LC emitted from the fiber coupler 1017 is guided to a detector 1021 by two optical fibers 1019, 1020, respectively.

The detector 1021 is, for example, a Balanced Photo Diode (hereinafter, referred as "BPD") that comprises a pair of photodetectors for detecting a pair of interfering lights LC respectively and thereby outputs a difference of detection results. The detector 1021 sends the detection result (detection signal) to the arithmetic control unit 12. The arithmetic control unit 12 forms cross-sectional images by applying the Fourier transformation, etc. to the spectral distribution based on the detection result obtained by the detector 1021, for example, for each of a series of wavelength scanning (per A line). The arithmetic control unit 12 causes a displaying portion 13 to display the formed image.

Although the Michelson interferometer is employed in this embodiment, it is possible to appropriately employ any type of interferometer, for example, Mach-Zehnder, etc.

FIG. 4 is a schematic diagram illustrating a displaying portion for displaying obtained OCT images and SLO images by the ophthalmologic microscope of the first embodiment.

As shown in FIG. 4, the displaying portion 13 comprises a display screen 1301. The display screen 1301 is provided with six image displaying portions 1302-1307. These image displaying portions are a first longitudinal section image displaying portion 1302, a cross-sectional image displaying portion 1303, a processed image displaying portion 1304, a front image displaying portion 1305, a second longitudinal section image displaying portion 1306, and a surgical guide image displaying portion 1307, respectively.

The front image displaying portion 1305 displays an image of fundus surface obtained by the SLO optical system, and the first longitudinal section image displaying portion 1302, the cross-sectional image displaying portion 1303, and the second longitudinal section image displaying portion 1306 display tomographic images of fundus obtained by the OCT optical system. The processed image displaying portion 1304 displays an image obtained by applying a predetermined processing treatment to images displayed on other image displaying portions (processed images), for example, angiography, projection (fundus tomographic image), an image for the detection of a lesion part such as a diabetic retinopathy. In FIG. 4, the processed image displaying portion 1304 displays the image of fundus surface obtained by the SLO optical system, with the section of lesion part being colored. Here, the section of lesion part is specified by image-analyzing the tomographic image obtained by the OCT.

As shown in FIG. 4, the front image displaying portion 1305 displays an observation image for fundus surface, with the lateral direction being x-axis and the longitudinal direction being y-axis. And the cross-sectional image displaying portion 1303 displays a tomographic image of fundus along the x-y cross section.

And the first longitudinal section image displaying portion 1302 and the second longitudinal section image displaying portion 1306 display tomographic images of fundus along two cross sections of z direction, which are indicated by a dotted line in the front image displaying portion 1305. The first longitudinal section image displaying portion 1302 displays a tomographic image of the y-z cross section and the second longitudinal section image displaying portion 1306 displays a tomographic image of the x-z cross section.

The surgical guide image displaying portion 1307 can display, for example, an image which is synthesized by superimposing a site in need of surgery on an image obtained before the surgery.

Here, in the ophthalmologic microscope of the first embodiment, there is no position mismatch between the observation image of fundus surface obtained by the SLO optical system and the tomographic image of fundus obtained by the OCT optical system, since the optical axis of the OCT optical system and the optical axis of the SLO optical system are coaxial. This allows for the accurate position alignment as there is no position mismatch between the observation image of fundus surface displayed on the front image displaying portion 1305 and the tomographic image of the x-y cross section displayed on the cross-sectional image displaying portion 1303. Also, it allows for the accurate position alignment as there is no position mismatch between two cross sections indicated by dotted lines at the front image displaying portion 1305, and the tomographic image of the y-z cross section displayed on the first longitudinal section image displaying portion 1302 and the tomographic image of the x-z cross section displayed on the second longitudinal section image displaying portion 1306.

FIG. 5 is a schematic diagram illustrating a shape of objective lens used for the ophthalmologic microscope of the first embodiment. FIG. 5 (A) is a view from the direction of the optical axis of the objective lens and FIG. 5 (B) is a cross-sectional view along the plane including the line AA' of FIG. 5 (A).

As shown in FIG. 5 (A), the objective lens 2 used in the first embodiment has a shape of circular lens with a hole 201 in its center. And the light path of the OCT optical system P-500 passes through that hole. And in the ophthalmologic microscope of the first embodiment, the light path of the observation optical system for left eye P-400L, the light path of the observation optical system for right eye P-400R, and the light path of the illuminating optical system P-300 respectively penetrates through different sections of the objective lens 2. Also, although not shown, the light path of the sub-observation optical system penetrates through in the proximity of the light path of the observation optical system for left eye P-400L.

Next, as shown in FIG. 5 (B), the sectional shape of the objective lens 2 has a shape of a convex lens with a hole in its center.

1-3. Shape of Objective Lens

Although a circular lens can be used as an objective lens for the ophthalmologic microscope of the present invention, it is preferable to decrease the angle formed by the optical axis of the OCT optical system and the optical axis of the observation optical system, and for this purpose the objective lens having a partial shape of circular lens or the objective lens having a shape of circular lens with a cutout or hole is preferably used.

In the present invention, "partial shape of circular lens" refers to a shape of circular lens which has been partially cut away in a plane view from the optical axis direction of the lens, and for example, but not limited to, the lens having a shape cut into a semicircular shape, a fan shape, a rectangular shape, etc. so that the light path of the observation optical system for left eye and the light path of the observation optical system for right eye penetrate through can be used.

Also, in the present invention, "shape of circular lens with a cutout or hole" refers to a shape with a cutout or hole in a plane view from the optical axis direction of the lens, and for example, but not limited to, the lens having a shape provided with a cutout or hole in a portion through which the light path of the OCT optical system penetrates can be used.

To ensure enough space to place optical elements of the OCT optical system, etc., the objective lens having a partial shape of circular lens is preferably used, rather than providing the circular lens with a cutout or hole.

Using a lens with such shape, the light path of the OCT optical system can pass through the cutaway portion where there is no lens exist in a circular lens, or through the cutout or hole provided in the lens. This allows to decrease the angle formed by the optical axis of the OCT optical system and the optical axis of the observation optical system without the optical axis of the OCT optical system penetrating through the objective lens.

In the present invention, the angle formed by the optical axis of the OCT optical system and the optical axis of the observation optical system (either of optical axes of the right and left observation light paths) may be preferably between 1 and 15°, more preferably between 4 and 10°, and yet preferably between 6 and 8°.

In the ophthalmologic microscope of the present invention, a circular lens or a lens consisting of part of a circular lens can be divided into two, and one of the divided lenses can be an objective lens through which the optical axis of the observation optical system penetrates and the other one of the divided lenses can be objective lens through which the optical axis of the OCT optical system penetrates.

Here, "lens consisting of part of a circular lens" can use lens having a "partial shape of circular lens" described above.

By using the divided lenses like this and making each of their positions independently controllable, it is possible to control the observation optical system and the OCT optical system independently.

1-4. Second Embodiment

Preferably, the OCT optical system can be additionally incorporated as an extension function into the ophthalmologic microscope comprising an observation optical system and an illuminating optical system. To additionally incorporate in this way, the inventors found that it can be compactly incorporated by bending the light path of the OCT optical system twice to adapt to the original function of the microscope.

That is, in the ophthalmologic microscope of the present invention, the OCT optical system preferably comprises:

a first optical member that guides a light from an OCT light source to a first optical axis direction;

a first reflecting member that guides the light guided to the first optical axis direction to a second optical axis direction substantially perpendicular to the first optical axis direction;

a second optical member that relays the light guided to the second optical axis direction;

a second reflecting member that guides the light relayed by the second optical member to a third optical axis direction substantially perpendicular to the second optical axis direction; and an objective lens for OCT that is placed on the third optical axis direction and irradiates a prescribed section of the subject's eye with the light guided to the third optical axis direction.

With this optical configuration, the OCT optical system can be compactly incorporated by adapting to the original function of the ophthalmologic microscope.

Hereinafter, examples of the embodiments of the ophthalmologic microscope of the present invention comprising the OCT optical system whose light path has been bended twice will be fully described in reference to drawings.

Figure 6:
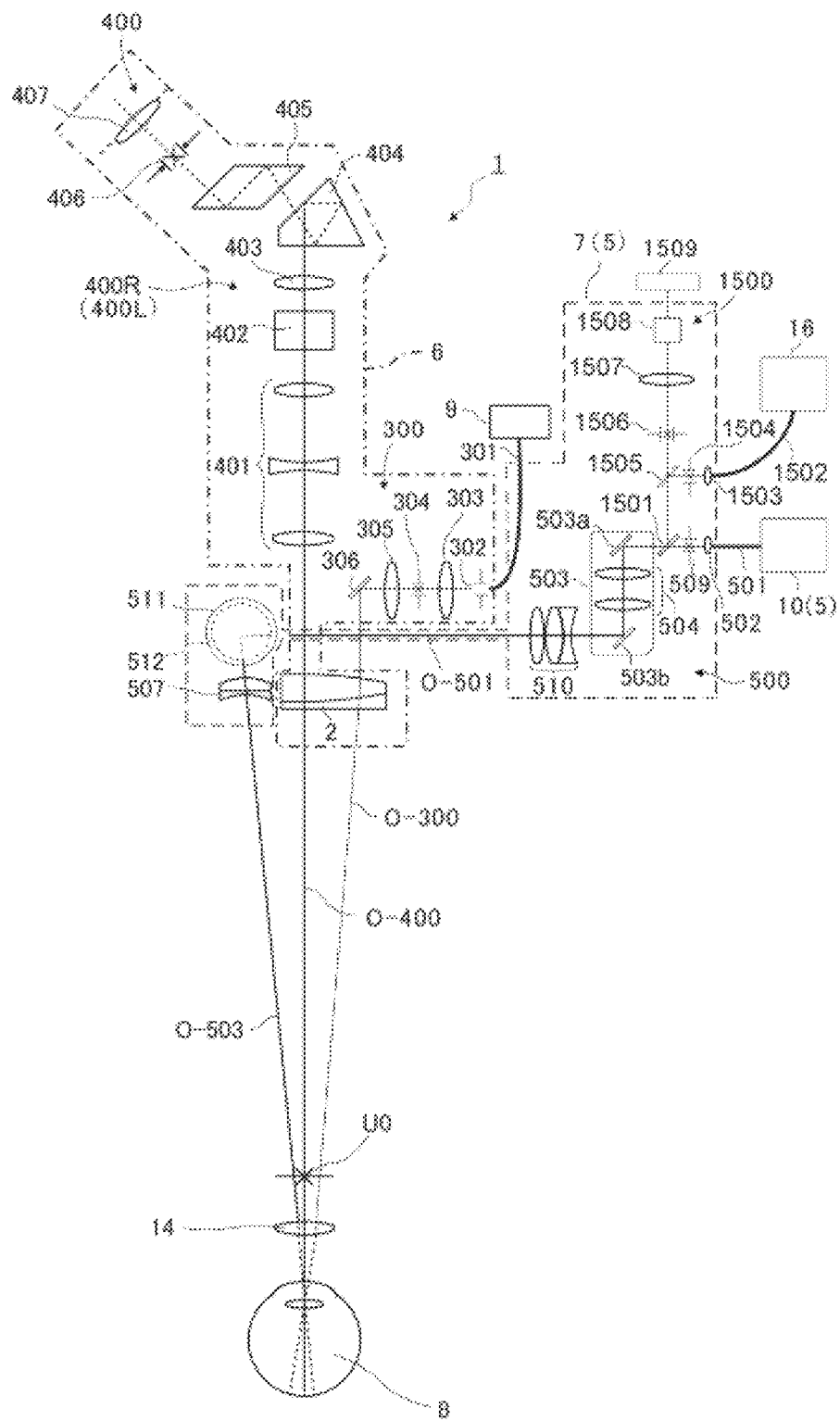
FIG. 6 schematically illustrates the configuration of an optical system taken from a side view, regarding to the ophthalmologic microscope of the second embodiment of the present invention.
Figure 7:
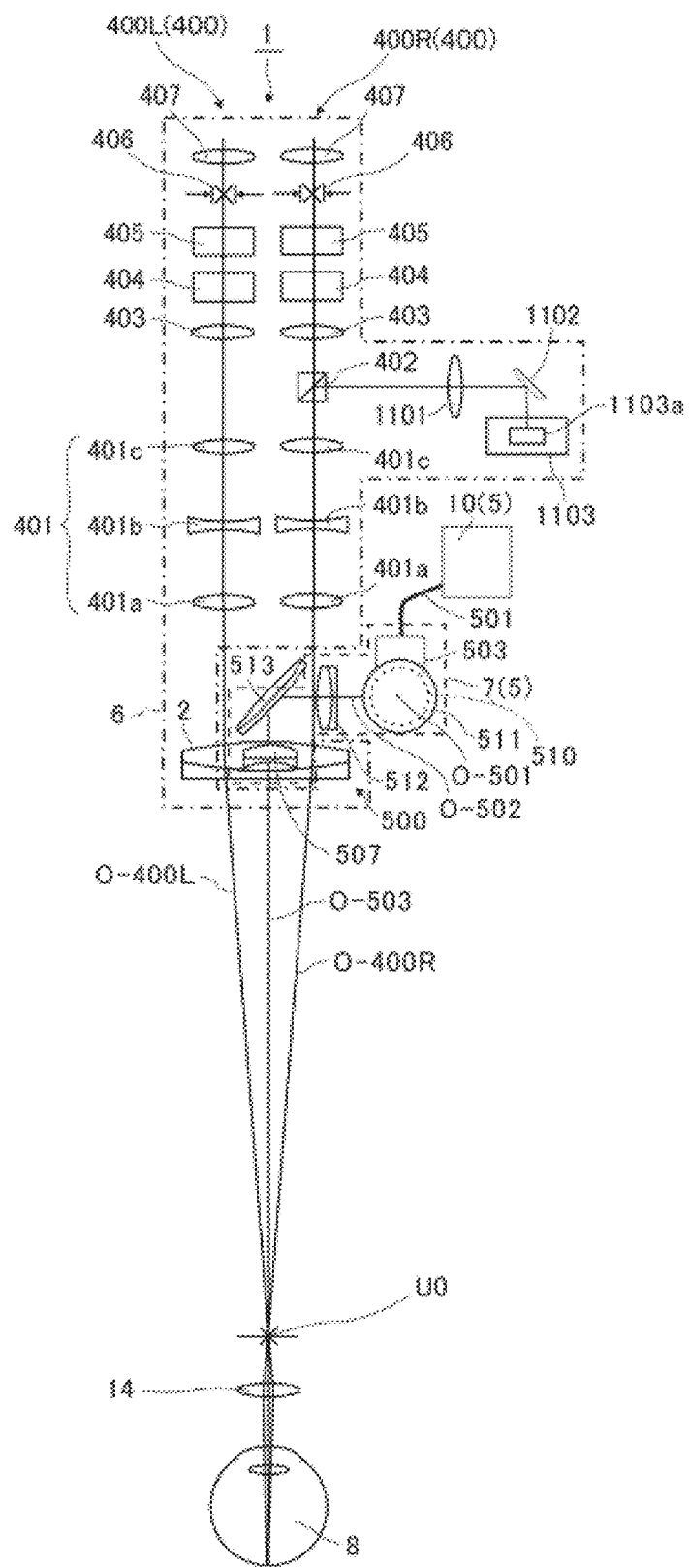
FIG. 7 schematically illustrates the configuration of an optical system taken from a front view, regarding to the ophthalmologic microscope of the second embodiment of the present invention.

FIGS. 6 and 7 schematically illustrate the second embodiment which is an example of the ophthalmologic microscope of the present invention.

FIG. 6 is a side schematic view of an ophthalmologic microscope 1, and FIG. 7 is a front schematic view of the same.

As shown in FIGS. 6 and 7, an OCT device 5 is arranged along with the ophthalmologic microscope 1.

The ophthalmologic microscope 1 is provided with an illuminating optical system 300 (not shown in FIG. 7), an observation optical system 400, and an OCT optical system 500.

The observation optical system 400 can observe a prescribed section of the subject's eye 8. As referenced in FIG. 6, the illuminating optical system 300 can illuminate a part of the subject's eye 8 to be observed.

The OCT device 5 arranged along with the ophthalmologic microscope 1 can obtain tomographic images of the subject's eye 8. The OCT optical system 500 is incorporated into the ophthalmologic microscope 1 as a part of the OCT device 5. The round-trip guide light path of the measuring light is constructed by the OCT optical system 500, the front-end lens 14, and the reflecting surface of the subject's eye 8 (cornea, retina, etc.).

As specified in FIG. 7, the observation optical system 400 comprises an observation optical system for right eye 400R and an observation optical system for left eye 400L. In FIG. 6, the entire configuration is shown for the observation optical system for right eye 400R, while only the objective lens 2 to be shared with the observation optical system for right eye 400R is shown for the observation optical system for left eye 400L.

Also, as specified in FIG. 7, the optical axis O-400R of the observation optical system for right eye 400R and the optical axis O-400L of the observation optical system for left eye 400L respectively pass through the objective lens 2.

In this embodiment, as shown in FIG. 6, the illuminating optical system 300 and the observation optical system 400 are accommodated in an ophthalmologic microscope body 6. Also, the OCT optical system 500 and the SLO optical system 1500 are accommodated in a function expansion unit 7. In FIGS. 6 and 7, the ophthalmologic microscope body 6 is indicated by a dashed-dotted line and the function expansion unit 7 is indicated by a dashed line.

The function expansion unit 7 is removably coupled to the ophthalmologic microscope body 6 via a joint (not shown).

As shown in FIGS. 6 and 7, the OCT device 5 consists of an OCT unit 10 and a function expansion unit 7.

The function expansion unit 7 accommodates an OCT optical system 500 and the SLO optical system 1500 (not shown in FIG. 7).

Figure 8:
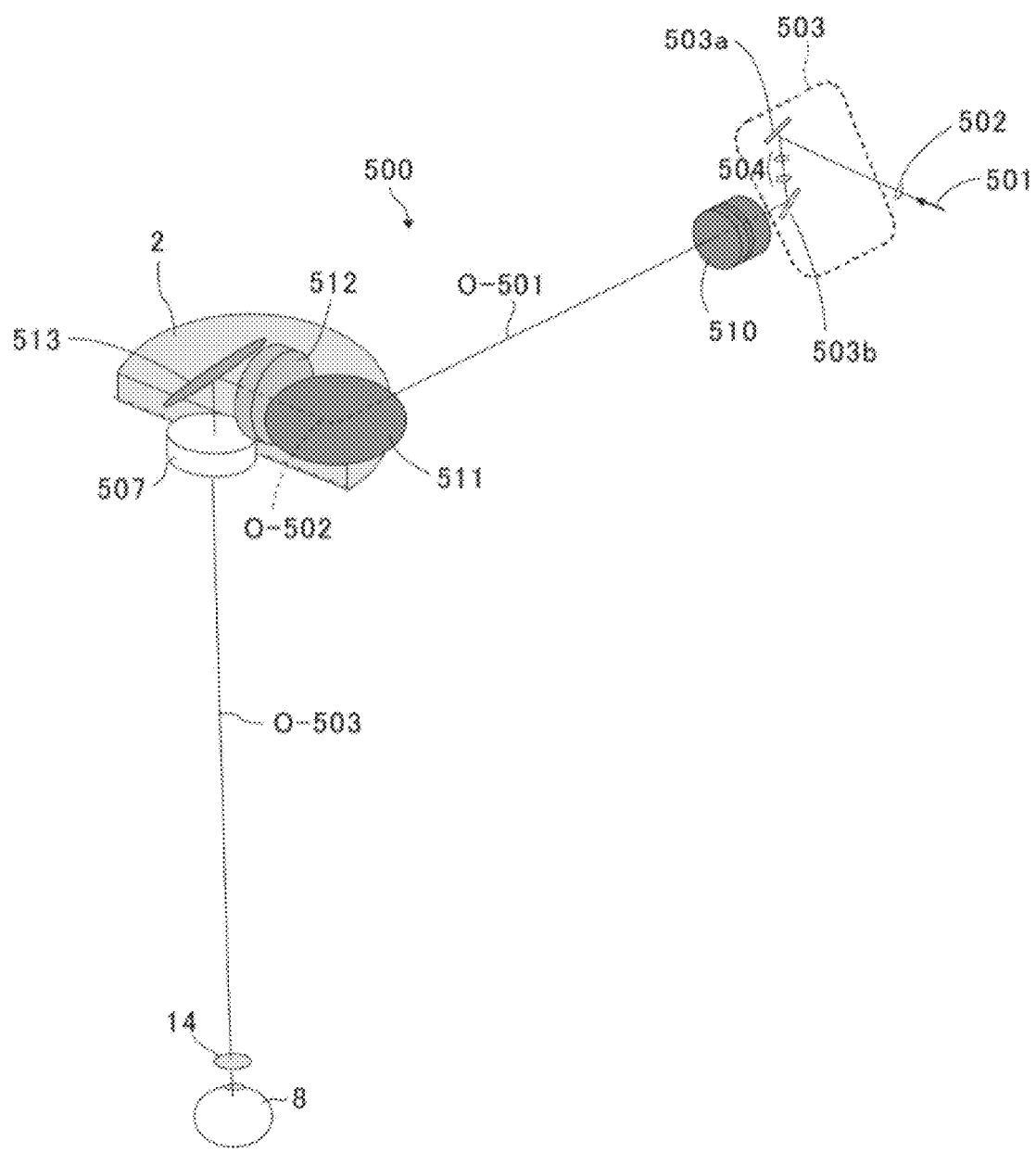
FIG. 8 is a perspective view of an OCT optical system, regarding to the ophthalmologic microscope of the second embodiment of the present invention.
Figure 9:
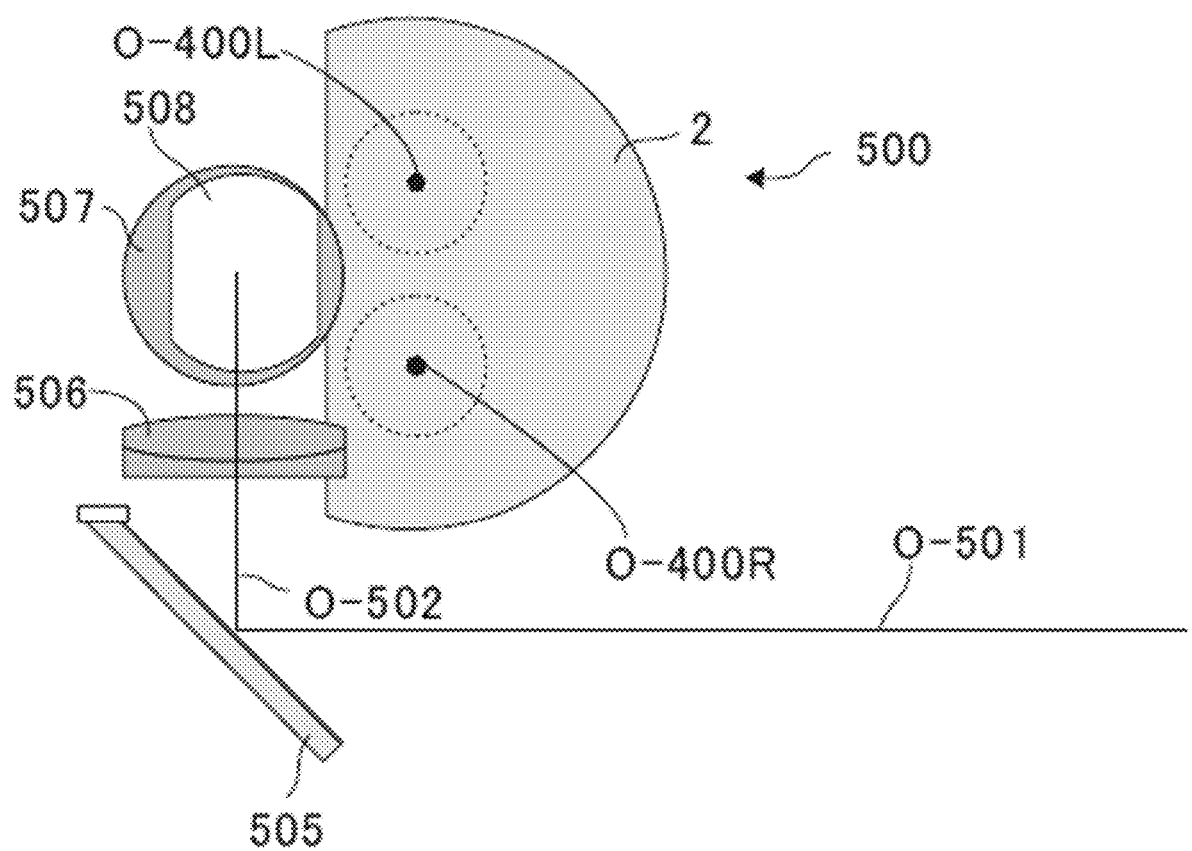
FIG. 9 is a plane view of an OCT optical system shown in FIG. 8, regarding to the ophthalmologic microscope of the second embodiment of the present invention.
Figure 10:
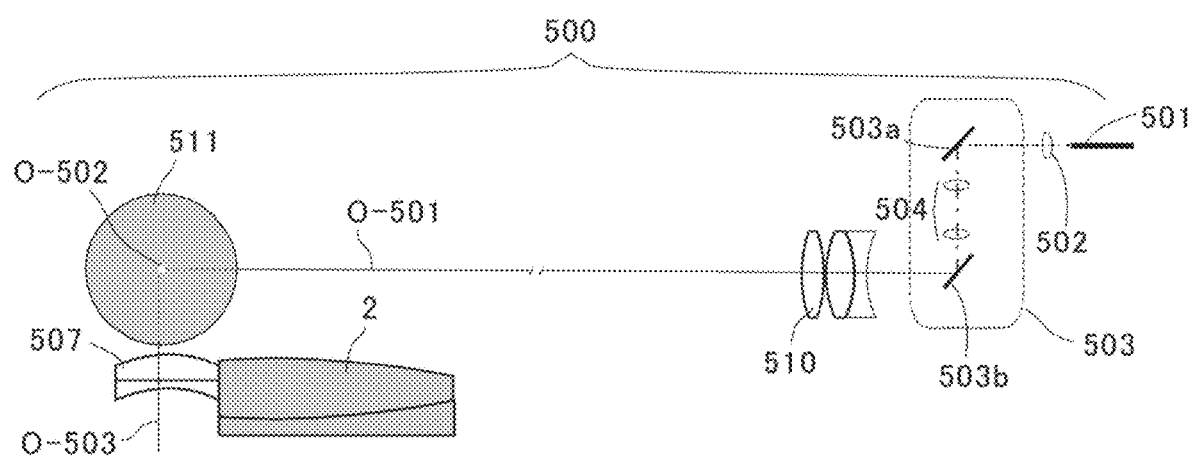
FIG. 10 is a side view of an OCT optical system shown in FIG. 8, regarding to the ophthalmologic microscope of the second embodiment of the present invention.
Figure 11:
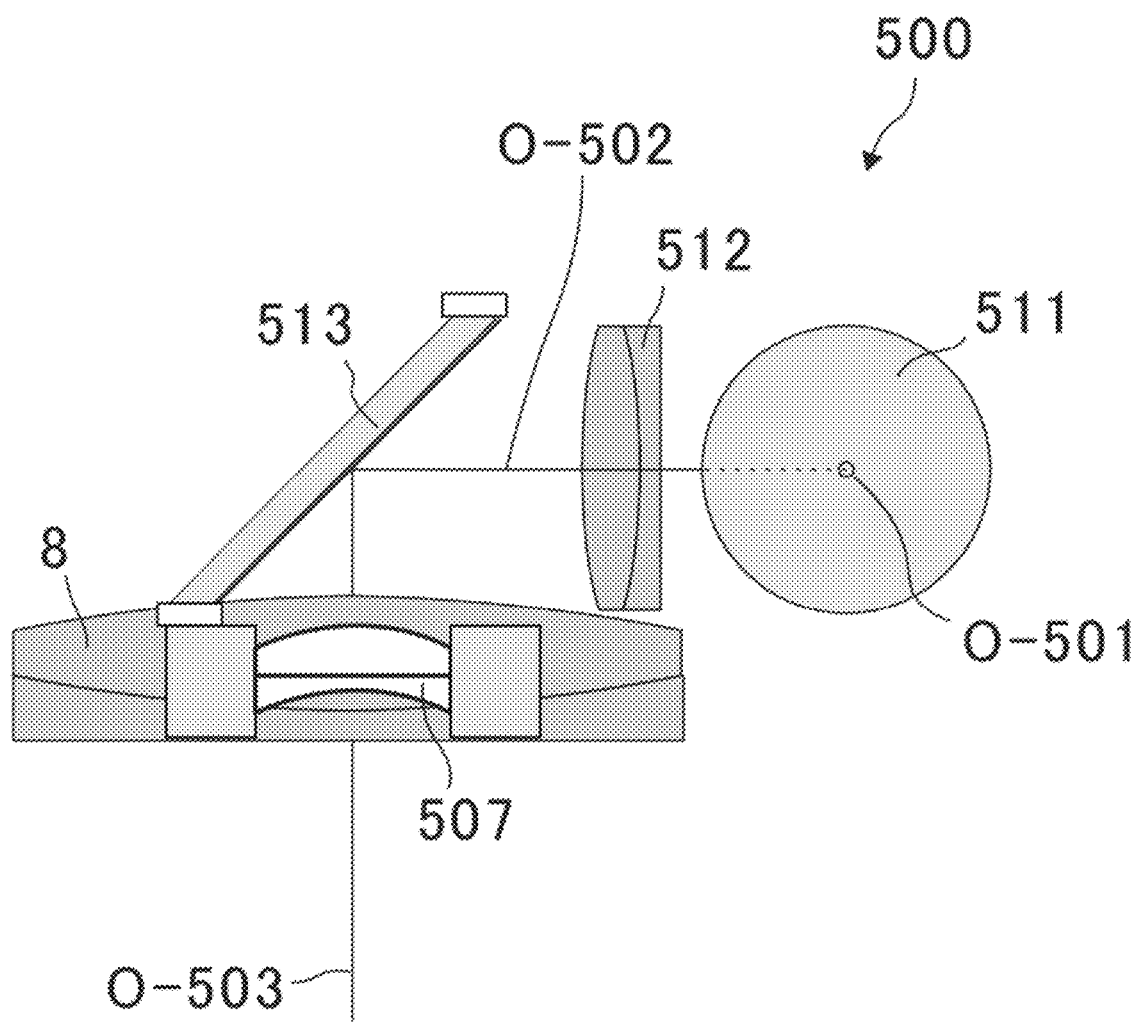
FIG. 11 is a front view of an OCT optical system shown in FIG. 8, regarding to the ophthalmologic microscope of the second embodiment of the present invention.

FIG. 8 is a perspective view of the OCT optical system 500, FIG. 9 is a plane view of the same, FIG. 10 is a side view of the same, and FIG. 11 is a front view of the same. However, in FIGS. 9 and 11, a collimating lens 502, a scanning function part 503, and a first optical member 510 (described below) are not shown.

In FIGS. 8 and 10, the OCT optical system 500 is configured to include a collimating lens 502, a scanning function part 503, a first optical member 510, a first reflecting member 511, a second optical member 512, a second reflecting member 513, and an objective lens for OCT 507.

The scanning function part 503 is a two-dimensional scanning mechanism that comprises optical scanners 503a, 503b. The scanning function part 503 is provided at the back side of the ophthalmologic microscope body 6 (the far side from an observer). The first optical member 510 is an OCT imaging lens that guides a light scanned by the scanning function part 503 to a direction of the first optical axis O-501. The first optical axis O-501 is formed from the far side to the near side at the position near the right outer side of the ophthalmologic microscope body 6 when viewing it from the front, and the light scanned by the scanning function part 503 is guided on the first optical axis O-501 from the far side to the near side.

As shown in FIGS. 8, 9, 10, and 11, the light guided on the first optical axis O-501 is guided to the direction of a second optical axis O-502 perpendicular to the direction of the first optical axis O-501 by the first reflecting member 511.

In this embodiment, as shown in FIG. 7, the second optical axis O-502 is formed so as to face inward from the right outer side of the ophthalmologic microscope body 6.

The second optical member 512 is placed on the second optical axis O-502, and the light passed through the second optical member 512 is reflected downward (direction substantially perpendicular to the second optical axis O-502) by the second reflecting member 513. This reflecting light path is indicated by the third optical axis direction O-503.

In this embodiment, the objective lens 2 has a partial shape of circular lens which has been cut away to have a cutting plane substantially parallel to the optical axis O-400, as shown in FIG. 6.

In this embodiment, the objective lens for OCT 507 is accommodated in the cutaway portion of this circular lens.

The light guided by the third optical axis direction O-503 is focused at a predetermined position on a side of the subject's eye 8 by the objective lens for OCT 507.

In FIGS. 6 and 7, the front side focal position U0 of the objective lens 2 is located before the subject's eye 8 and the front-end lens 14 is placed between the subject's eye 8 and the front side focal position U0.

The front-end lens 14 is a lens used when observing a retina at the fundus of the eye, and it is inserted onto optical axes O-300, O-400L, O-400R, O-503 right in front of the subject's eye by a moving means (not shown). In this case, the front side focal position U0 of the objective lens 2 is conjugate to the retina at the fundus of eye. Also, when observing an anterior eye part such as a cornea, an iris, etc., the observation is performed by eliminating the front-end lens 14 from right in front of the subject's eye 8.

As described above, the optical axis O-503 of the OCT optical system 500 passes through the objective lens for OCT 507 and it is away from the optical axis O-400 of the observation optical system 400.

Therefore, the OCT optical system 500 and the observation optical system 400 are independent of each other.

As shown in FIG. 6, the SLO optical system 1500 is configured to include a SLO light source 16, an optical fiber 1502, a collimating lens 1503, an illuminating field diaphragm 1504, a dichroic mirror 1501, a half mirror 1505, an optical diaphragm 1506, a condensing lens 1507, a reflected light detector 1508, and an image generation part 1509.

The SLO light source 16 is provided outside of the function expansion unit 7 but coupled with it by being connected to the one end of the optical fiber 1502. The light ray generated by the SLO light source 16 emits from the other end of the optical fiber 1502. The emitted light ray is reflected at the half mirror 1505 by way of the collimating lens 1503, the illuminating field diaphragm 1504, and also reflected at the dichroic mirror 1501 to converge coaxially to the measuring light of the OCT optical system 500.

As shown in FIG. 1, the converged light ray of the SLO optical system 1500 is two-dimensionally scanned at the optical scanners 503a, 503b same as the measuring light of the OCT optical system 500. The function expansion unit 7 can be downsized/produced at a lower cost by commonly using the optical scanners 503a, 503b that require a complex mechanism, at the OCT optical system 500 and the SLO optical system 1500.

Also in the ophthalmologic microscope of the second embodiment, there is no position mismatch between the observation image of fundus surface obtained by the SLO optical system and the tomographic image of fundus obtained by the OCT optical system, since the optical axis of the OCT optical system and the optical axis of the SLO optical system are coaxial. As shown in FIG. 4, this allows for the accurate position alignment as there is no position mismatch between the observation image of fundus surface displayed on the front image displaying portion 1305 and the tomographic image of the x-y cross section displayed on the cross-sectional image displaying portion 1303. Also, it allows for the accurate position alignment as there is no position mismatch between two cross sections indicated by dotted lines in the front image displaying portion 1305, and the tomographic image of the y-z cross section displayed on the first longitudinal section image displaying portion 1302 and the tomographic image of the x-z cross section displayed on the second longitudinal section image displaying portion 1306.

1-5. Third Embodiment

Figure 12A:
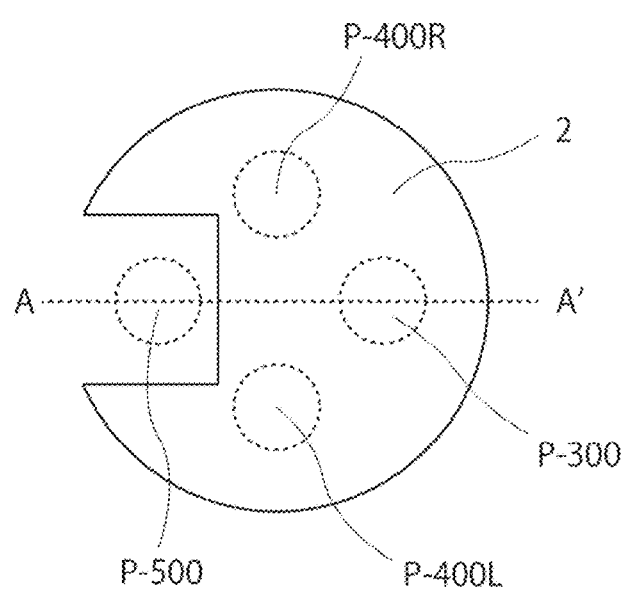
FIG. 12 schematically illustrates a shape of an objective lens used for the ophthalmologic microscope of the third embodiment of the present invention.
Figure 12B:
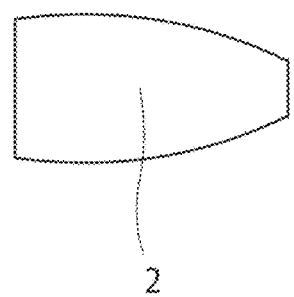

A shape of an objective lens used in the third embodiment which is other example of the ophthalmologic microscope of the present invention is shown in FIG. 12. FIG. 12 (A) illustrates an objective lens seen from the optical axis direction and FIG. 12 (B) is a cross-sectional view of FIG. 12 (A) in the plane including a line AA'.

As shown in FIG. 12 (A), the objective lens 2 used in the third embodiment has a shape of circular lens with a partial cutout. And, the light path of the OCT optical system P-500 passes through that cutout portion.

And, as shown in FIG. 12 (B), the sectional shape of the objective lens 2 has a partial shape of convex lens which has been partially cut away.

1-6. Fourth Embodiment

Figure 13A:
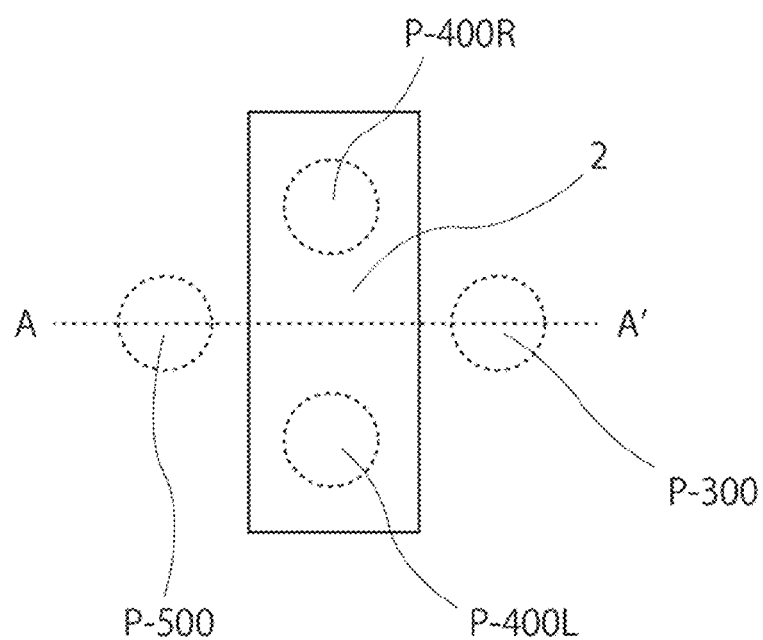
FIG. 13 schematically illustrates a shape of an objective lens used for the ophthalmologic microscope of the fourth embodiment of the present invention.
Figure 13B:
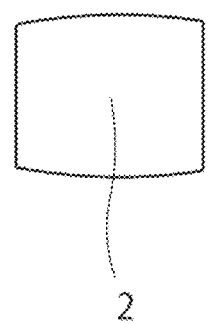

A shape of an objective lens used in the fourth embodiment which is other example of the ophthalmologic microscope of the present invention is shown in FIG. 13. FIG. 13 (A) illustrates an objective lens seen from the optical axis direction and FIG. 13 (B) is a cross-sectional view of FIG. 13 (A) in the plane including a line AA'.

As shown in FIG. 13 (A), the objective lens 2 used in the fourth embodiment has a shape of circular lens which has been partially cut away in a rectangular shape, and the light path of the observation optical system for left eye P-400L and the light path of observation optical system for right eye P-400R respectively penetrate through different sections of the objective lens 2. And the light path of the OCT optical system P-500 and the light path of the illuminating optical system P-300 pass through in the proximity of the objective lens 2.

And, as shown in FIG. 13 (B), the sectional shape of the objective lens 2 has a partial shape of convex lens which has been partially cut away.

1-7. Fifth Embodiment

Figure 14A:
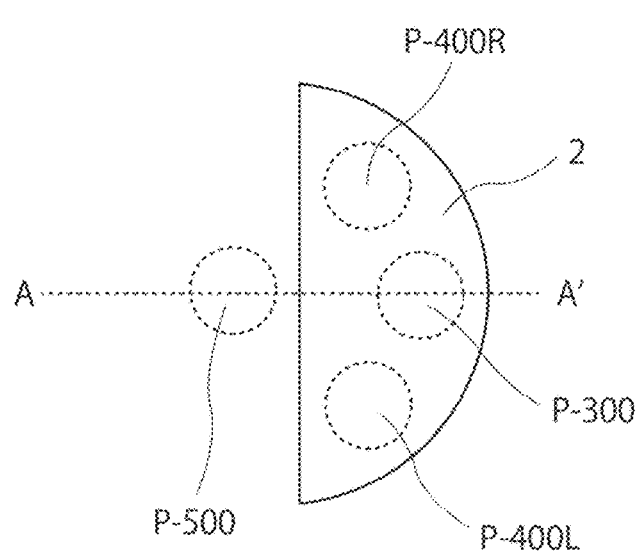
Figure 14B:
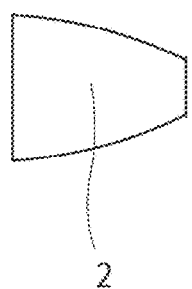

A shape of an objective lens used in the fifth embodiment which is other example of the ophthalmologic microscope of the present invention is shown in FIG. 14. FIG. 14 (A) illustrates an objective lens seen from the optical axis direction and FIG. 14 (B) is a cross-sectional view FIG. 14(A) in the plane including a line AA'.

As shown in FIG. 14 (A), the objective lens 2 used in the fifth embodiment has a shape of circular lens which has been partially cut away in a semicircular shape, and the light path of the observation optical system for left eye P-400L, the light path of the observation optical system for right eye P-400R, and the light path of the illuminating optical system P-300 respectively penetrate through different sections of the objective lens 2. And the light path of the OCT optical system P-500 passes through in the proximity of the objective lens 2.

And, as shown in FIG. 14 (B), the sectional shape of the objective lens 2 has a partial shape of convex lens which has been partially cut away.

1-8. Sixth Embodiment

Figure 15A:
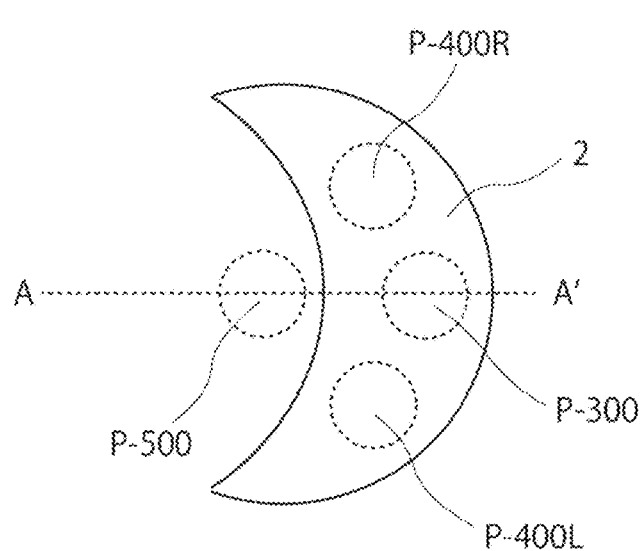
FIG. 15 schematically illustrates a shape of an objective lens used for the ophthalmologic microscope of the sixth embodiment of the present invention.
Figure 15B:
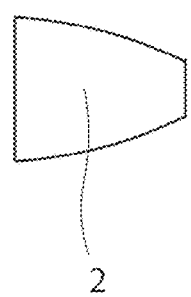

A shape of an objective lens used in the sixth embodiment which is other example of the ophthalmologic microscope of the present invention is shown in FIG. 15. FIG. 15 (A) illustrates an objective lens seen from the optical axis direction and FIG. 15 (B) is a cross-sectional view of FIG. 15 (A) in the plane including a line AA'.

As shown in FIG. 15 (A), the objective lens 2 used in the sixth embodiment has a shape of circular lens which has been partially cut away in a crescentic shape, and the light path of the observation optical system for left eye P-400L, the light path of the observation optical system for right eye P-400R, and the light path of the illuminating optical system P-300 respectively penetrate through different sections of the objective lens 2. And the light path of the OCT optical system P-500 passes through in the proximity of the objective lens 2.

And, as shown in FIG. 15 (B), the sectional shape of the objective lens 2 has a partial shape of convex lens which has been partially cut away.

1-9. Seventh Embodiment

Figure 16A:
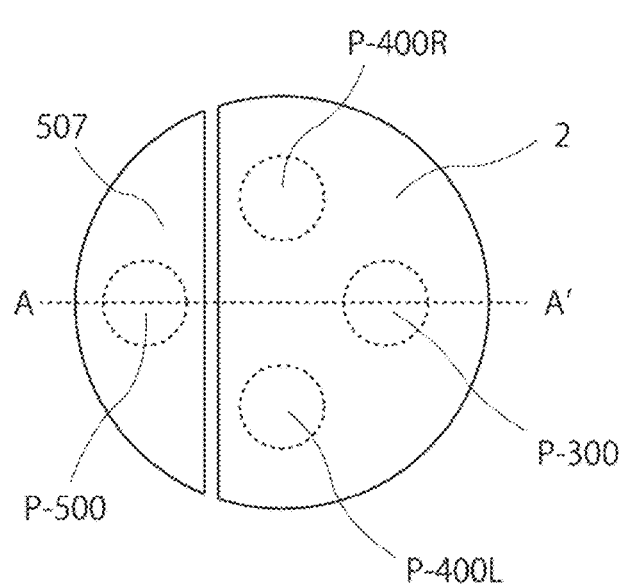
FIG. 16 schematically illustrates a shape of an objective lens used for the ophthalmologic microscope of the seventh embodiment of the present invention.
Figure 16B:
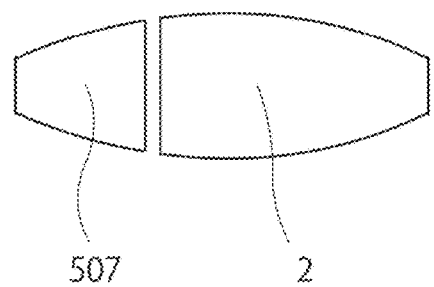
Figure 17:
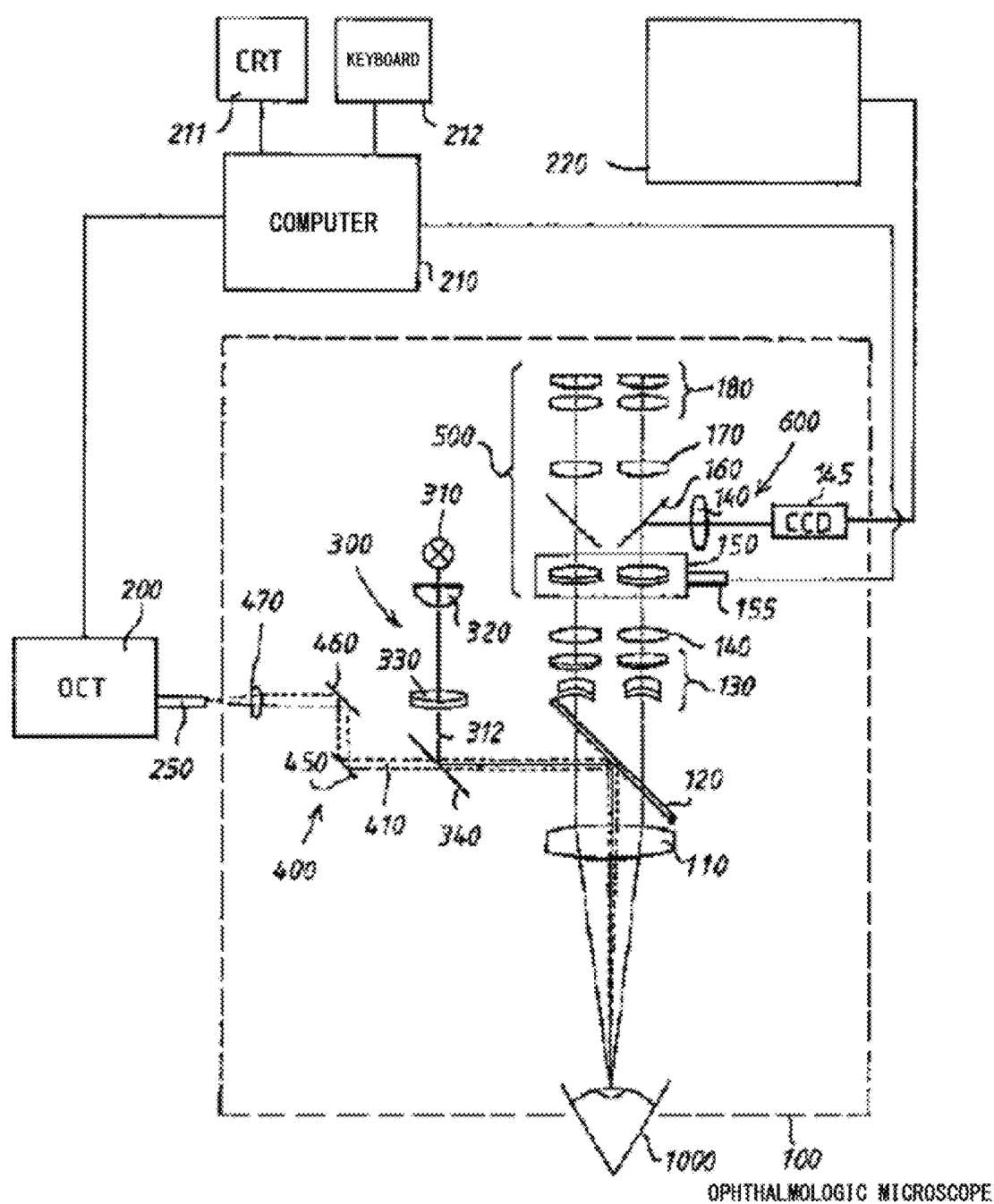
FIG. 17 is a drawing cited from FIG. 1 of Patent document 1.
Figure 18:
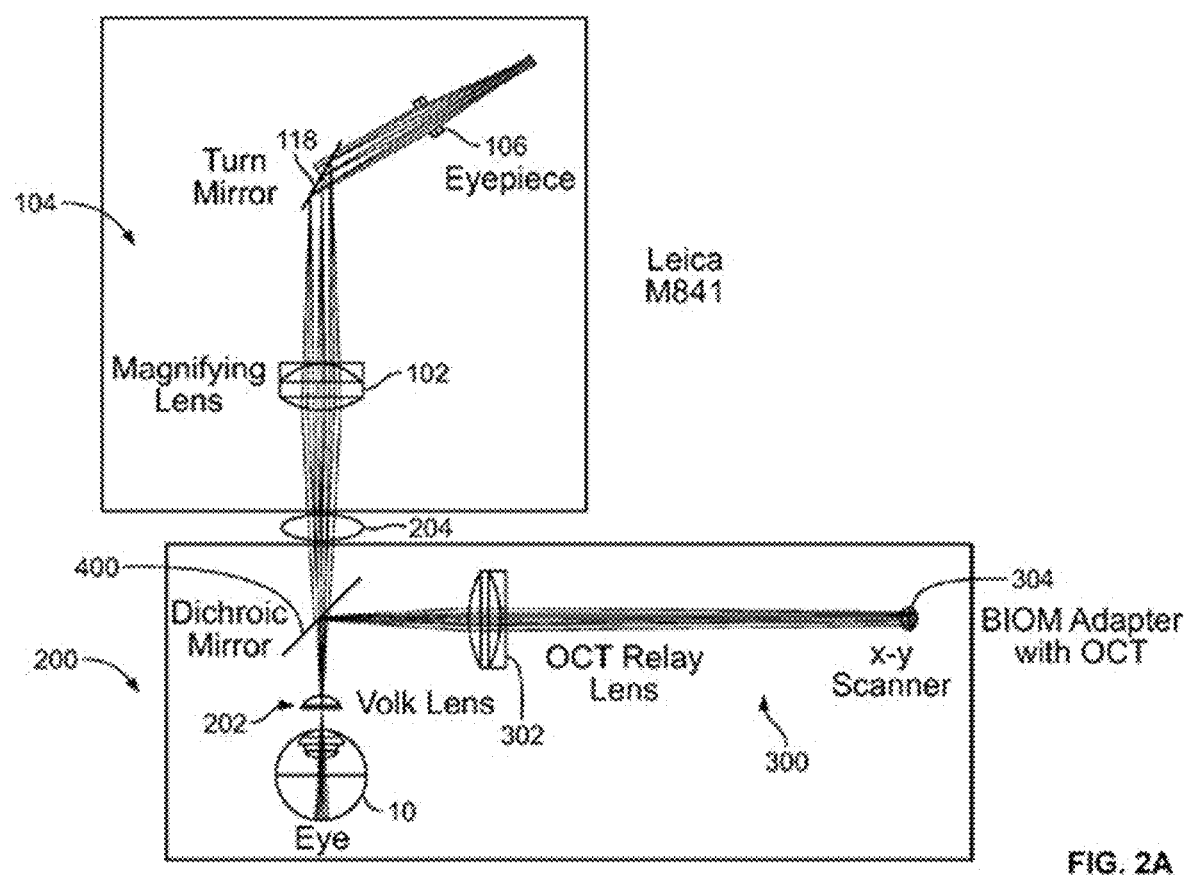
FIG. 18 is a drawing cited from FIG. 2A of Patent document 6.

Shapes of an objective lens and an objective lens for OCT used in the seventh embodiment which is other example of the ophthalmologic microscope of the present invention is shown in FIG. 16. FIG. 16 (A) illustrates an objective lens seen from the optical axis direction and FIG. 16 (B) is a cross-sectional view of FIG. 16 (A) in the plane including a line AA'.

As shown in FIG. 16 (A), the objective lens and the objective lens for OCT used in the seventh embodiment is a circular lens divided in two. One of the divided lenses 2 is used as an objective lens, through which the light path of the observation optical system for left eye P-400L, the light path of the observation optical system for right eye P-400R, and the light path of the illuminating optical system P-300 penetrate. The other one of the divided lenses 507 is used as an objective lens for OCT, through which the light path of the OCT optical system P-500 penetrates.

Also, as shown in FIG. 16 (B), the sectional shape of the objective lens 2 and the objective lens for OCT 507 is a shape of convex lens divided in two.

2. Function Expansion Unit

The function expansion unit of the present invention is detachable to the ophthalmologic microscope and capable of adding functions of the OCT to the ophthalmologic microscope.

The function expansion unit of the present invention is used for an ophthalmologic microscope comprising an illuminating optical system for illuminating a subject's eye, an observation optical system that comprises the light path of an observation optical system for left eye and the light path of an observation optical system for right eye to observe the subject's eye illuminated by the illuminating optical system, and an objective lens through which the optical axis of the observation optical system for left eye and the optical axis of the observation optical system for right eye of the observation optical system commonly penetrate.

And, the function expansion unit of the present invention comprises, a joint detachable against the ophthalmologic microscope, an OCT optical system for scanning a measuring light to test the subject's eye with Optical Coherence Tomography, and a SLO optical system that scans a light ray which is a visible ray, a near infrared ray, or an infrared ray and guides the light to the subject's eye, characterized in that the optical axis of the OCT optical system does not penetrate through the objective lens through which the optical axis of the observation optical system penetrates, and the optical axis of the observation optical system and the optical axis of the OCT optical system are non-coaxial when the function expansion unit is attached to the ophthalmologic microscope via the joint, wherein the optical axis of the OCT optical system and the optical axis of the SLO optical system are substantially coaxial, and the ophthalmologic microscope can observe a section of the subject's where the OCT optical system scans, with the SLO optical system.

The OCT optical system for the function expansion unit of the present invention is independent from the observation optical system for the ophthalmologic microscope, thereby allows for unitization and is effective in increasing the degree of freedom in the optical design. Also, as the function expansion unit of the present invention is detachable to the ophthalmologic microscope via a joint, it is effective in readily adding functions of the OCT to the ophthalmologic microscope. Also, the function expansion unit of the present invention comprises a SLO optical system that guides a light ray substantially coaxial with the optical axis of the OCT optical system to the subject's eye, thereby is effective in observing the subject's eye without a mismatch from an image obtained by the OCT optical system.

"Joint" in the function expansion unit of the present invention is not particularly limited as long as it makes the function expansion unit detachable to the ophthalmologic microscope, and can be, for example, but not limited to, a joint for coupling by a fitting or a joint for coupling by using a screw.

A concrete example of the function expansion unit of the present invention is as described as the function expansion unit in the ophthalmologic microscope of the first embodiment and the ophthalmologic microscope of the second embodiment (portion indicated by the symbol 7 in FIGS. 1, 6, and 7 which is surrounded by the dashed-dotted lines).

3. Function Expansion Set

The function expansion set of the present invention is a set including the function expansion unit described in 2 above and the objective lens for replacement for replacing objective lens of the ophthalmologic microscope.

Here, the objective lens having a shape described in 1-3 above can be used as an objective lens for replacement.

A concrete example of the objective lens for replacement can include the objective lens used in the first embodiment and the third or seventh embodiment above (FIGS. 5 and 12-16).

As the function expansion set of the present invention is detachable to the ophthalmologic microscope via a joint, it is effective in readily adding functions of the OCT to the ophthalmologic microscope. Also, the function expansion set of the present invention comprises a SLO optical system that guides a light ray substantially coaxial with the optical axis of the OCT optical system to the subject's eye, thereby is effective in observing the subject's eye without a mismatch from an image obtained by the OCT optical system.

INDUSTRIAL APPLICABILITY

The ophthalmologic microscope, the function expansion unit, the function expansion set of the present invention are useful in the industry of manufacturing ophthalmic medical equipment.

EXPLANATION OF SYMBOLS

Symbols used in FIGS. 1-16 will be explained below:
1 ophthalmologic microscope
2 objective lens
300 illuminating optical system
301 optical fiber
302 emitted light diaphragm
303 condenser lens
304 illuminating field diaphragm
305 collimating lens
306 reflecting mirror
400 observation optical system
400L observation optical system for left eye
400R observation optical system for right eye
400S sub-observation optical system
401 variable magnification lens system
401a, 401b, 401c zoom lens
402 beam splitter
403 imaging lens
404 image erecting prism
405 eye width adjusting prism
406 field diaphragm
407 eyepiece lens
408 prism
408a reflecting surface of prism
409 imaging lens
410 reflecting mirror
411 eyepiece lens for assistant
5 OCT device
500 OCT optical system
501 optical fiber
502 collimating lens
503 scanning function part
503a, 503b optical scanner
504 relay optical system
505 first lens group
506 second lens group
507 objective lens for OCT
508 reflecting mirror
509 illuminating field diaphragm
510 first optical member
511 first reflecting member
512 second optical member
513 second reflecting member
6 ophthalmologic microscope body
7 function expansion unit
8 subject's eye
8a retina
9 illuminating light source
10 OCT unit
1001 OCT light source unit
1002 optical fiber
1003 polarized wave controller
1004 optical fiber
1005 fiber coupler
1006 optical fiber
1007 collimator
1008 light path length correction member
1009 dispersion compensation member
1010 corner cube
1011 collimator
1012 optical fiber
1013 polarized wave controller
1014 optical fiber
1015 attenuator
1016 optical fiber
1017 fiber coupler
1018 optical fiber
1019 optical fiber
1020 optical fiber
1021 detector
1101 imaging lens
1102 reflecting mirror
1103 television camera
1103a imaging element
12 arithmetic control unit
13 displaying portion
1301 display screen
1302 first longitudinal section image displaying portion
1303 cross-sectional image displaying portion
1304 processed image displaying portion
1305 front image displaying portion
1306 second longitudinal section image displaying portion
1307 surgical guide image displaying portion
14 front-end lens
1500 SLO optical system
1501 dichroic mirror
1502 optical fiber
1503 collimating lens
1504 illuminating field diaphragm
1505 half mirror
1506 optical diaphragm
1507 condensing lens
1508 reflected light detector
1509 image generation part
16 SLO light source
O-300 optical axis of illuminating optical system
O-400 optical axis of observation optical system
O-400L optical axis of observation optical system for left eye
O-400R optical axis of observation optical system for right eye
O-400S optical axis of sub-observation optical system
O-500 optical axis of OCT optical system, optical axis of SLO optical system
O-501 first optical axis
O-502 second optical axis
O-503 third optical axis
P-300 light path of illuminating optical system
P-400L light path of observation optical system for left eye
P-400R light path of observation optical system for right eye
P-500 light path of OCT optical system, light path of SLO optical system
L0 light output from OCT light source unit
LC interfering light
LS measuring light
LR reference light
U0 front side focal position

The invention claimed is:

1. A function expansion unit for an ophthalmologic microscope comprising:
   an illuminating optical system for illuminating a subject's eye;
   an observation optical system comprising an observation optical system for a left eye and an observation optical system fora right eye to observe the subject's eye illuminated by the illuminating optical system;
   an objective lens through which the optical axis of the observation optical system for the left eye and the optical axis of the observation optical system for the right eye of the observation optical system commonly penetrate;
   a joint detachable against the ophthalmologic microscope;
   an OCT optical system for scanning a measuring light to test the subject's eye with Optical Coherence Tomography; and
   an SLO optical system that scans a light ray which is a visible ray, a near infrared ray, or an infrared ray and guides the light to the subject's eye,
   wherein the optical axis of the OCT optical system does not penetrate through the objective lens through which the optical axis of the observation optical system penetrates, and the optical axis of the observation optical system and the optical axis of the OCT optical system are non-coaxial, when the function expansion unit is attached to the ophthalmologic microscope via the joint, and
   wherein the optical axis of the OCT optical system and the optical axis of the SLO optical system are substantially coaxial, and the ophthalmologic microscope can observe a section of the subject's eye where the OCT optical system scans, with the SLO optical system.

2. The function expansion unit according to claim 1, wherein the OCT optical system comprises:
   a first optical member that guides a light from an OCT light source to a first optical axis direction;
   a first reflecting member that guides the light guided to the first optical axis direction to a second optical axis direction substantially perpendicular to the first optical axis direction;
   a second optical member that relays the light guided to the second optical axis direction;
   a second reflecting member that guides the light relayed by the second optical member to a third optical axis direction substantially perpendicular to the second optical axis direction; and
   an objective lens for OCT that is placed on the third optical axis direction and irradiates a prescribed section of the subject's eye with the light guided to the third optical axis direction.

3. The function expansion unit according to claim 1, further comprising a deflection optical element that commonly scans a measuring light of the OCT optical system and a light ray of the SLO optical system.

4. A function expansion set for an ophthalmologic microscope comprising:
   a function expansion unit comprising:
      an illuminating optical system for illuminating a subject's eye;
      an observation optical system comprising an observation optical system for a left eye and an observation optical system for a right eye to observe the subject's eye illuminated by the illuminating optical system;
      an objective lens through which the optical axis of the observation optical system for the left eye and the optical axis of the observation optical system for the right eye of the observation optical system commonly penetrate;
      a joint detachable against the ophthalmologic microscope;
      an OCT optical system for scanning a measuring light to test the subject's eye with Optical Coherence Tomography; and
      an SLO optical system that scans a light ray which is a visible ray, a near infrared ray, or an infrared ray and guides the light to the subject's eye,
      wherein the optical axis of the OCT optical system does not penetrate through the objective lens through which the optical axis of the observation optical system penetrates, and the optical axis of the observation optical system and the optical axis of the OCT optical system are non-coaxial, when the function expansion unit is attached to the ophthalmologic microscope via the joint, and
      wherein the optical axis of the OCT optical system and the optical axis of the SLO optical system are substantially coaxial, and the ophthalmologic microscope can observe a section of the subject's eye where the OCT optical system scans, with the SLO optical system; and
   a replacement objective lens to replace the objective lens in the function expansion unit.

5. The function expansion unit according to claim 4, wherein the replacement objective lens has either a partial shape of a circular lens or a shape of circular lens with a cutout or hole, wherein, when replacing the objective lens with the replacement objective lens and attaching the function expansion unit to the ophthalmologic microscope via the joint, the optical axis of the OCT optical system penetrates through a portion where the replacement objective lens does not exist, or through a cutout or hole provided in the replacement objective lens.

* * * * *